(12) United States Patent
Kohlbrecher et al.

(10) Patent No.: US 10,311,972 B2
(45) Date of Patent: Jun. 4, 2019

(54) MEDICAL DEVICE SYSTEM PERFORMANCE INDEX

(71) Applicant: ICU Medical, Inc., San Clemente, CA (US)

(72) Inventors: Christopher Egan Kohlbrecher, Poway, CA (US); Jonathan Leigh Walton, Escondido, CA (US); Daniel Chien-Yu Hsu, San Diego, CA (US); Michael Paul Myers, San Diego, CA (US)

(73) Assignee: ICU Medical, Inc., San Clemente, CA (US)

( * ) Notice: Subject to any disclaimer, the term of this patent is extended or adjusted under 35 U.S.C. 154(b) by 482 days.

(21) Appl. No.: 14/538,545

(22) Filed: Nov. 11, 2014

(65) Prior Publication Data

US 2015/0134265 A1 May 14, 2015

Related U.S. Application Data

(60) Provisional application No. 61/902,504, filed on Nov. 11, 2013.

(51) Int. Cl.
*G16H 40/63* (2018.01)
*G16H 10/60* (2018.01)
(Continued)

(52) U.S. Cl.
CPC ......... *G16H 40/63* (2018.01); *G06F 11/3006* (2013.01); *G06F 11/3409* (2013.01);
(Continued)

(58) Field of Classification Search
None
See application file for complete search history.

(56) References Cited

U.S. PATENT DOCUMENTS

| 4,024,864 A | 5/1977 | Davies et al. |
| 4,055,175 A | 10/1977 | Clemens et al. |

(Continued)

FOREIGN PATENT DOCUMENTS

| CA | 2 060 151 | 8/1997 |
| CA | 2 125 300 | 10/1999 |

(Continued)

OTHER PUBLICATIONS

Matsunaga, A. & Fortes, J. a. B. On the Use of Machine Learning to Predict the Time and Resources Consumed by Applications. In IEEE/ACM International Conference on Cluster, Cloud and Grid Computing (CCGrid) 495-504 (2010).*

(Continued)

*Primary Examiner* — Soren Harward
(74) *Attorney, Agent, or Firm* — Knobbe, Martens, Olson & Bear, LLP

(57) ABSTRACT

A distributed network system and method includes a processing unit configured to manage safety data for a plurality of medical devices, a database software component in communication with the processing unit, and a monitoring software component in communication with the processing unit. The monitoring software component is configured to monitor a number of messages between a number of medical devices and the processing unit, to process performance parameters to generate an overall performance index, and to generate an output that is viewable by a user. The output includes relative contributions of each of the performance parameters to the overall performance index, where the overall performance index is generated using a weighting factor associated with each of the performance parameters. The performance parameters include the number of messages waiting to be processed, which has the largest weight-
(Continued)

ing factor, and a disk queue length, which has the smallest weighting factor.

23 Claims, 8 Drawing Sheets

(51) Int. Cl.
    *G06F 11/30*            (2006.01)
    *G06F 11/34*            (2006.01)
    *G16H 40/40*            (2018.01)
    *G06F 19/00*            (2018.01)
    *G16H 20/17*            (2018.01)
    *A61M 5/142*            (2006.01)

(52) U.S. Cl.
    CPC ............ *G06F 19/00* (2013.01); *G06F 19/326* (2013.01); *G06F 19/3468* (2013.01); *G16H 10/60* (2018.01); *G16H 40/40* (2018.01); *A61M 5/142* (2013.01); *G06F 11/3065* (2013.01); *G06F 11/3442* (2013.01); *G06F 11/3452* (2013.01); *G06F 11/3457* (2013.01); *G16H 20/17* (2018.01)

(56) References Cited

U.S. PATENT DOCUMENTS

| | | | |
|---|---|---|---|
| 4,151,845 A | 5/1979 | Clemens | |
| 4,213,454 A | 7/1980 | Shim | |
| 4,240,438 A | 12/1980 | Updike et al. | |
| 4,280,494 A | 7/1981 | Cosgrove et al. | |
| 4,308,866 A | 1/1982 | Jeliffe | |
| 4,370,983 A | 2/1983 | Lichtenstein et al. | |
| 4,373,527 A | 2/1983 | Fischell | |
| 4,392,849 A | 7/1983 | Petre et al. | |
| 4,395,259 A | 7/1983 | Prestele et al. | |
| 4,457,751 A | 7/1984 | Rodler | |
| 4,464,170 A | 8/1984 | Clemens | |
| 4,469,481 A | 9/1984 | Kobayashi | |
| 4,475,901 A | 10/1984 | Kraegen et al. | |
| 4,494,950 A | 1/1985 | Fischell | |
| 4,498,843 A | 2/1985 | Schneider et al. | |
| 4,515,584 A | 5/1985 | Abe et al. | |
| 4,526,568 A | 7/1985 | Clemens et al. | |
| 4,529,401 A | 7/1985 | Leslie et al. | |
| 4,543,955 A | 10/1985 | Schroeppel | |
| 4,551,133 A | 11/1985 | Zegers de Beyl et al. | |
| 4,553,958 A | 11/1985 | LeCocq | |
| 4,559,037 A | 12/1985 | Franetzki et al. | |
| 4,613,937 A | 9/1986 | Batty | |
| 4,624,661 A | 11/1986 | Arimond | |
| 4,633,878 A | 1/1987 | Bombardieri | |
| 4,634,426 A | 1/1987 | kamen | |
| 4,634,427 A | 1/1987 | Hannula et al. | |
| 4,674,652 A | 6/1987 | Aten et al. | |
| 4,676,776 A | 6/1987 | Howson et al. | |
| 4,679,562 A | 7/1987 | Luksha | |
| 4,685,903 A | 8/1987 | Cable et al. | |
| 4,695,954 A | 9/1987 | Rose | |
| 4,696,671 A | 9/1987 | Epstein et al. | |
| 4,714,462 A | 12/1987 | DiDomenico | |
| 4,722,734 A | 2/1988 | Kolin | |
| 4,731,051 A | 3/1988 | Fischell | |
| 4,741,732 A | 5/1988 | Crankshaw et al. | |
| 4,756,706 A | 7/1988 | Kerns et al. | |
| 4,776,842 A | 10/1988 | Franetzki et al. | |
| 4,785,969 A | 11/1988 | McLaughlin | |
| 4,803,625 A | 2/1989 | Fu et al. | |
| 4,835,372 A | 5/1989 | Gombrich et al. | |
| 4,838,275 A | 6/1989 | Lee | |
| 4,838,856 A | 6/1989 | Mulreany et al. | |
| 4,838,857 A | 6/1989 | Strowe et al. | |
| 4,854,324 A | 8/1989 | Hirschman et al. | |
| 4,857,716 A | 8/1989 | Gombrich et al. | |
| 4,858,154 A | 8/1989 | Anderson et al. | |
| 4,898,578 A | 2/1990 | Rubalcaba, Jr. | |
| 4,908,017 A | 3/1990 | Howson et al. | |
| 4,933,873 A | 6/1990 | Kaufman et al. | |
| 4,943,279 A | 7/1990 | Samiotes et al. | |
| 4,946,439 A | 8/1990 | Eggers | |
| 4,953,745 A | 9/1990 | Rowlett | |
| 4,978,335 A | 12/1990 | Arthur, III | |
| 5,000,739 A | 3/1991 | Kulisz et al. | |
| 5,010,473 A | 4/1991 | Jacobs | |
| 5,014,698 A | 5/1991 | Cohen | |
| 5,016,172 A | 5/1991 | Dessertine | |
| 5,026,084 A | 6/1991 | Paisfield | |
| 5,034,004 A | 7/1991 | Crankshaw | |
| 5,041,086 A | 8/1991 | Koenig et al. | |
| 5,058,161 A | 10/1991 | Weiss | |
| 5,078,683 A | 1/1992 | Sancoff et al. | |
| 5,084,828 A | 1/1992 | Kaufman et al. | |
| 5,088,981 A | 2/1992 | Howson et al. | |
| 5,097,505 A | 3/1992 | Weiss | |
| 5,100,380 A | 3/1992 | Epstein et al. | |
| 5,102,392 A | 4/1992 | Sakai et al. | |
| 5,104,374 A | 4/1992 | Bishko et al. | |
| 5,109,850 A | 5/1992 | Blanco et al. | |
| 5,131,816 A | 7/1992 | Brown | |
| 5,142,484 A | 8/1992 | Kaufman et al. | |
| 5,153,827 A | 10/1992 | Coutre et al. | |
| 5,157,640 A | 10/1992 | Backner | |
| 5,161,222 A | 11/1992 | Montejo et al. | |
| 5,177,993 A | 1/1993 | Beckman et al. | |
| 5,181,910 A | 1/1993 | Scanlon | |
| 5,190,522 A | 3/1993 | Wocicki et al. | |
| 5,199,439 A | 4/1993 | Zimmerman et al. | |
| 5,200,891 A | 4/1993 | Kehr et al. | |
| 5,216,597 A | 6/1993 | Beckers | |
| 5,221,268 A | 6/1993 | Barton et al. | |
| 5,230,061 A | 7/1993 | Welch | |
| 5,243,982 A | 9/1993 | Möstl et al. | |
| 5,244,463 A | 9/1993 | Cordner, Jr. et al. | |
| 5,249,260 A | 9/1993 | Nigawara et al. | |
| 5,256,156 A | 10/1993 | Kern et al. | |
| 5,256,157 A | 10/1993 | Samiotes et al. | |
| 5,261,702 A | 11/1993 | Mayfield | |
| 5,317,506 A | 5/1994 | Coutre et al. | |
| 5,319,355 A | 6/1994 | Russek | |
| 5,319,363 A | 6/1994 | Welch et al. | |
| 5,330,634 A | 7/1994 | Wong et al. | |
| 5,338,157 A | 8/1994 | Blamquist | |
| 5,341,476 A | 8/1994 | Lowell | |
| 5,364,346 A | 11/1994 | Schrezenmeir | |
| 5,366,346 A | 11/1994 | Danby | |
| 5,368,562 A | 11/1994 | Blomquist et al. | |
| 5,373,454 A | 12/1994 | Kanda et al. | |
| 5,376,070 A | 12/1994 | Purvis et al. | |
| 5,378,231 A | 1/1995 | Johnson et al. | |
| 5,389,071 A | 2/1995 | Kawahara et al. | |
| 5,389,078 A | 2/1995 | Zalesky et al. | |
| 5,417,222 A | 5/1995 | Dempsey et al. | |
| 5,423,748 A | 6/1995 | Uhala | |
| 5,429,602 A | 7/1995 | Hauser | |
| 5,431,627 A | 7/1995 | Pastrone et al. | |
| 5,432,777 A | 7/1995 | Le Boudec et al. | |
| 5,445,621 A | 8/1995 | Poli et al. | |
| 5,447,164 A | 9/1995 | Shaya et al. | |
| 5,455,851 A | 10/1995 | Chaco et al. | |
| 5,461,365 A | 10/1995 | Schlager et al. | |
| 5,464,392 A | 11/1995 | Epstein et al. | |
| 5,465,082 A | 11/1995 | Chaco | |
| 5,485,408 A | 1/1996 | Blomquist | |
| 5,486,286 A | 1/1996 | Peterson et al. | |
| 5,493,430 A | 2/1996 | Lu et al. | |
| 5,496,273 A | 3/1996 | Pastrone et al. | |
| 5,505,828 A | 4/1996 | Wong et al. | |
| 5,507,288 A | 4/1996 | Bocker et al. | |
| 5,507,786 A | 4/1996 | Morgan et al. | |
| 5,508,499 A | 4/1996 | Ferrario | |
| 5,515,713 A | 5/1996 | Saugues et al. | |
| 5,520,637 A | 5/1996 | Pager et al. | |
| 5,522,798 A | 6/1996 | Johnson et al. | |

(56) References Cited

U.S. PATENT DOCUMENTS

| | | |
|---|---|---|
| 5,547,470 A | 8/1996 | Johnson et al. |
| 5,554,013 A | 9/1996 | Owens et al. |
| 5,562,615 A | 10/1996 | Nassif |
| 5,577,169 A | 11/1996 | Prezioso |
| 5,582,323 A | 12/1996 | Kurtenbach |
| 5,582,593 A | 12/1996 | Hultman |
| 5,594,786 A | 1/1997 | Chaco et al. |
| 5,598,519 A | 1/1997 | Narayanan |
| 5,620,608 A | 4/1997 | Rosa et al. |
| 5,630,710 A | 5/1997 | Tune et al. |
| 5,636,044 A | 6/1997 | Yuan et al. |
| 5,643,212 A | 7/1997 | Coutre et al. |
| 5,651,775 A | 7/1997 | Walker et al. |
| 5,658,131 A | 8/1997 | Aoki et al. |
| 5,658,250 A | 8/1997 | Blomquist et al. |
| 5,665,065 A | 9/1997 | Colman et al. |
| 5,669,877 A | 9/1997 | Blomquist |
| 5,672,154 A | 9/1997 | Sillén et al. |
| 5,681,285 A | 10/1997 | Ford et al. |
| 5,685,844 A | 11/1997 | Marttila |
| 5,687,717 A | 11/1997 | Halpern et al. |
| 5,689,229 A | 11/1997 | Chaco et al. |
| 5,697,899 A | 12/1997 | Hillman et al. |
| 5,699,509 A | 12/1997 | Gary et al. |
| 5,713,856 A | 2/1998 | Eggers et al. |
| 5,718,562 A | 2/1998 | Lawless et al. |
| 5,719,761 A | 2/1998 | Gatti et al. |
| 5,733,259 A | 3/1998 | Valcke et al. |
| 5,738,102 A | 4/1998 | Lemelson |
| 5,744,027 A | 4/1998 | Connell et al. |
| 5,752,621 A | 5/1998 | Passamante |
| 5,754,111 A | 5/1998 | Garcia |
| 5,764,034 A | 6/1998 | Bowman et al. |
| 5,764,159 A | 6/1998 | Neftel et al. |
| 5,772,635 A | 6/1998 | Dastur et al. |
| 5,774,865 A | 6/1998 | Glynn |
| 5,778,256 A | 7/1998 | Darbee |
| 5,778,345 A | 7/1998 | McCartney |
| 5,781,442 A | 7/1998 | Engleson et al. |
| 5,782,805 A | 7/1998 | Meinzer et al. |
| 5,788,669 A | 8/1998 | Peterson |
| 5,797,515 A | 8/1998 | Liff et al. |
| 5,800,387 A | 9/1998 | Duffy et al. |
| 5,814,015 A | 9/1998 | Gargano et al. |
| 5,822,544 A | 10/1998 | Chaco et al. |
| 5,822,715 A | 10/1998 | Worthington et al. |
| 5,827,179 A | 10/1998 | Lichter et al. |
| 5,832,448 A | 11/1998 | Brown |
| 5,836,910 A | 11/1998 | Duffy et al. |
| 5,850,344 A | 12/1998 | Conkright |
| 5,867,821 A | 2/1999 | Ballantyne et al. |
| 5,870,733 A | 2/1999 | Bass et al. |
| 5,871,465 A | 2/1999 | Vasko |
| 5,873,731 A | 2/1999 | Predergast |
| 5,885,245 A | 3/1999 | Lynch et al. |
| 5,897,493 A | 4/1999 | Brown |
| 5,897,498 A | 4/1999 | Canfield, II et al. |
| 5,910,252 A | 6/1999 | Truitt et al. |
| 5,912,818 A | 6/1999 | McGrady et al. |
| 5,915,240 A | 6/1999 | Karpf |
| 5,920,054 A | 7/1999 | Uber, III |
| 5,920,263 A | 7/1999 | Huttenhoff et al. |
| 5,924,074 A | 7/1999 | Evans |
| 5,931,764 A | 8/1999 | Freeman et al. |
| 5,935,099 A | 8/1999 | Peterson et al. |
| 5,935,106 A | 8/1999 | Olsen |
| 5,941,846 A | 8/1999 | Duffy et al. |
| 5,956,501 A | 9/1999 | Brown |
| 5,957,885 A | 9/1999 | Bollish et al. |
| 5,960,085 A | 9/1999 | de la Huerga |
| 5,961,448 A | 10/1999 | Swenson et al. |
| 5,967,559 A | 10/1999 | Abramowitz |
| 5,971,594 A | 10/1999 | Sahai et al. |
| 5,975,081 A | 11/1999 | Hood et al. |
| 5,990,838 A | 11/1999 | Burns et al. |
| 5,997,476 A | 12/1999 | Brown |
| 6,000,828 A | 12/1999 | Leet |
| 6,003,006 A | 12/1999 | Colella et al. |
| 6,012,034 A | 1/2000 | Hamparian et al. |
| 6,017,318 A | 1/2000 | Gauthier et al. |
| 6,021,392 A | 2/2000 | Lester et al. |
| 6,024,539 A | 2/2000 | Blomquist |
| 6,032,155 A | 2/2000 | de la Huerga |
| 6,032,676 A | 3/2000 | Moore |
| 6,073,106 A | 6/2000 | Rozen et al. |
| 6,104,295 A | 8/2000 | Gaisser et al. |
| 6,112,182 A | 8/2000 | Akers et al. |
| RE36,871 E | 9/2000 | Epstein et al. |
| 6,115,390 A | 9/2000 | Chuah |
| 6,122,536 A | 9/2000 | Sun et al. |
| 6,126,637 A | 10/2000 | Kriesel et al. |
| 6,135,949 A | 10/2000 | Russo et al. |
| 6,150,942 A | 11/2000 | O'Brien |
| 6,151,643 A | 11/2000 | Chong et al. |
| 6,157,914 A | 12/2000 | Seto et al. |
| 6,159,147 A | 12/2000 | Lichter et al. |
| 6,167,567 A | 12/2000 | Chiles et al. |
| 6,182,667 B1 | 2/2001 | Hanks et al. |
| 6,189,105 B1 | 2/2001 | Lopes |
| 6,195,589 B1 | 2/2001 | Ketcham |
| 6,208,974 B1 | 3/2001 | Campbell et al. |
| 6,222,323 B1 | 4/2001 | Yamashita et al. |
| 6,223,440 B1 | 5/2001 | Rashman |
| 6,226,277 B1 | 5/2001 | Chuah |
| 6,227,371 B1 | 5/2001 | Song |
| 6,234,176 B1 | 5/2001 | Domae et al. |
| 6,241,704 B1 | 6/2001 | Peterson et al. |
| 6,248,067 B1 | 6/2001 | Causey, III et al. |
| 6,249,705 B1 | 6/2001 | Snell |
| 6,257,265 B1 | 7/2001 | Brunner et al. |
| 6,259,355 B1 | 7/2001 | Chaco et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,280,380 B1 | 8/2001 | Bardy |
| 6,283,761 B1 | 9/2001 | Joao |
| 6,285,665 B1 | 9/2001 | Chuah |
| 6,292,860 B1 | 9/2001 | Cochcroft, Jr. |
| 6,312,378 B1 | 11/2001 | Bardy |
| 6,327,254 B1 | 12/2001 | Chuah |
| 6,330,008 B1 * | 12/2001 | Razdow ............ G06F 11/3404 709/230 |
| 6,339,718 B1 | 1/2002 | Zatezalo et al. |
| 6,346,886 B1 | 2/2002 | de la Huerga |
| 6,363,282 B1 | 3/2002 | Nichols et al. |
| 6,371,719 B1 | 4/2002 | Hildebrandt |
| 6,377,548 B1 | 4/2002 | Chuah |
| 6,388,951 B1 | 5/2002 | Matsumoto et al. |
| 6,406,426 B1 | 6/2002 | Reuss et al. |
| 6,408,330 B1 | 6/2002 | de la Huerga |
| 6,418,334 B1 | 7/2002 | Unger et al. |
| 6,427,088 B1 | 7/2002 | Bowman et al. |
| 6,428,483 B1 | 8/2002 | Carlebach |
| 6,442,432 B2 | 8/2002 | Lee |
| 6,469,991 B1 | 10/2002 | Chuah |
| 6,475,180 B2 | 11/2002 | Peterson et al. |
| 6,482,158 B2 | 11/2002 | Mault |
| 6,485,418 B2 | 11/2002 | Yasushi et al. |
| 6,494,694 B2 | 12/2002 | Lawless et al. |
| 6,494,831 B1 | 12/2002 | Koritzinsky |
| 6,497,680 B1 | 12/2002 | Holst et al. |
| 6,514,460 B1 | 2/2003 | Fendrock |
| 6,517,482 B1 | 2/2003 | Eiden et al. |
| 6,519,569 B1 | 2/2003 | White et al. |
| 6,520,930 B2 | 2/2003 | Critchlow et al. |
| 6,540,672 B1 | 4/2003 | Simonsen et al. |
| 6,542,902 B2 | 4/2003 | Dulong et al. |
| 6,544,212 B2 | 4/2003 | Galley et al. |
| 6,544,228 B1 | 4/2003 | Heitmeier |
| 6,546,350 B1 | 4/2003 | Hartmann et al. |
| 6,551,276 B1 | 4/2003 | Mann et al. |
| 6,554,798 B1 | 4/2003 | Mann et al. |
| 6,558,320 B1 | 5/2003 | Causey et al. |

(56) References Cited

U.S. PATENT DOCUMENTS

| | | |
|---|---|---|
| 6,558,351 B1 | 5/2003 | Steil et al. |
| 6,565,509 B1 | 5/2003 | Say et al. |
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |
| 6,589,229 B1 | 7/2003 | Connelly et al. |
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Crnkovich et al. |
| 6,780,156 B2 | 8/2004 | Haueter et al. |
| 6,790,198 B1 | 9/2004 | White et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogora |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,936,029 B2 | 8/2005 | Mann et al. |
| 6,945,954 B2 | 9/2005 | Hochman et al. |
| 6,948,492 B2 | 9/2005 | Wemeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 | 8/2007 | Staehr et al. |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |
| 7,343,224 B2 | 3/2008 | DiGianfilippo et al. |
| 7,346,025 B2 | 3/2008 | Bryson |
| 7,347,836 B2 | 3/2008 | Peterson et al. |
| 7,354,420 B2 | 4/2008 | Steil et al. |
| 7,369,897 B2 | 5/2008 | Boveja et al. |
| 7,369,948 B1 | 5/2008 | Ferenczi et al. |
| 7,383,088 B2 | 6/2008 | Spinelli et al. |
| 7,384,410 B2 | 6/2008 | Eggers et al. |
| 7,398,183 B2 | 7/2008 | Holland et al. |
| 7,399,277 B2 | 7/2008 | Saidara et al. |

(56) References Cited

U.S. PATENT DOCUMENTS

| | | |
|---|---|---|
| 7,402,153 B2 | 7/2008 | Steil et al. |
| 7,420,472 B2 | 9/2008 | Tran |
| 7,432,807 B2 | 10/2008 | Schmitt |
| 7,447,643 B1 | 11/2008 | Olson |
| 7,454,314 B2 | 11/2008 | Holland et al. |
| 7,457,804 B2 | 11/2008 | Uber, III et al. |
| 7,464,040 B2 | 12/2008 | Joao |
| 7,471,994 B2 | 12/2008 | Ford et al. |
| 7,483,756 B2 | 1/2009 | Engleson et al. |
| 7,489,808 B2 | 2/2009 | Gerder |
| 7,490,021 B2 | 2/2009 | Holland et al. |
| 7,490,048 B2 | 2/2009 | Joao |
| 7,491,187 B2 | 2/2009 | Van Den Berghe et al. |
| 7,523,401 B1 | 4/2009 | Aldridge |
| 7,524,304 B2 | 4/2009 | Genosar |
| 7,551,078 B2 | 6/2009 | Carlson |
| 7,559,321 B2 | 7/2009 | Wermeling et al. |
| 7,565,197 B2 | 7/2009 | Haulbrich et al. |
| 7,572,230 B2 | 8/2009 | Neumann et al. |
| 7,578,802 B2 | 8/2009 | Hickle |
| 7,621,009 B2 | 11/2009 | Elhabashy |
| D606,533 S | 12/2009 | De Jong et al. |
| 7,636,718 B1 | 12/2009 | Steen et al. |
| 7,640,172 B2 | 12/2009 | Kuth |
| 7,645,258 B2 | 1/2010 | White et al. |
| 7,647,237 B2 | 1/2010 | Malave et al. |
| 7,662,124 B2 | 2/2010 | Duchon et al. |
| 7,668,731 B2 | 2/2010 | Martucci et al. |
| 7,671,733 B2 | 3/2010 | McNeal |
| 7,678,071 B2 | 3/2010 | Lebel et al. |
| 7,687,678 B2 | 3/2010 | Jacobs |
| 7,697,994 B2 | 4/2010 | VanDanacker et al. |
| 7,698,239 B2 | 4/2010 | Lieuallen |
| 7,705,727 B2 | 4/2010 | Pestotnik |
| 7,724,147 B2 | 5/2010 | Brown et al. |
| 7,739,126 B1 | 6/2010 | Cave |
| 7,746,218 B2 | 6/2010 | Collins, Jr. |
| 7,766,873 B2 | 8/2010 | Moberg et al. |
| 7,776,029 B2 | 8/2010 | Whitehurst et al. |
| 7,776,031 B2 | 8/2010 | Hartlaub et al. |
| 7,785,313 B2 | 8/2010 | Mastrototaro |
| 7,806,852 B1 | 10/2010 | Jurson |
| 7,806,886 B2 | 10/2010 | Kanderian, Jr. et al. |
| 7,826,981 B2 | 11/2010 | Goode, Jr. et al. |
| 7,835,927 B2 | 11/2010 | Schlotterbeck et al. |
| 7,836,314 B2 | 11/2010 | Chieu |
| 7,856,276 B2 | 12/2010 | Ripart et al. |
| 7,860,583 B2 | 12/2010 | Condurso et al. |
| 7,868,754 B2 | 1/2011 | Salvat, Jr. |
| 7,871,394 B2 | 1/2011 | Halbert et al. |
| 7,886,231 B2 | 2/2011 | Hopermann et al. |
| 7,895,053 B2 | 2/2011 | Holland et al. |
| 7,896,842 B2 | 3/2011 | Palmroos et al. |
| 7,899,546 B2 | 3/2011 | Sieracki et al. |
| 7,905,710 B2 | 3/2011 | Wang et al. |
| 7,920,061 B2 | 4/2011 | Klein et al. |
| 7,933,780 B2 | 4/2011 | De La Huerga |
| 7,938,796 B2 | 5/2011 | Moubayed |
| 7,945,452 B2 | 5/2011 | Fathallah et al. |
| 7,974,714 B2 | 7/2011 | Hoffberg |
| 7,996,241 B2 | 8/2011 | Zak |
| 8,034,026 B2 | 10/2011 | Grant |
| 8,038,593 B2 | 10/2011 | Friedman et al. |
| 8,048,040 B2 | 11/2011 | Kiani |
| 8,060,576 B2 | 11/2011 | Chan et al. |
| 8,065,161 B2 | 11/2011 | Howard et al. |
| 8,066,672 B2 | 11/2011 | Mandro |
| 8,078,983 B2 | 12/2011 | Davis et al. |
| 8,082,018 B2 | 12/2011 | Duchon et al. |
| 8,082,312 B2 | 12/2011 | Chan et al. |
| 8,147,448 B2 | 4/2012 | Sundar et al. |
| 8,149,131 B2 | 4/2012 | Blornquist |
| 8,169,914 B2 | 5/2012 | Bajpai |
| 8,171,094 B2 | 5/2012 | Chan et al. |
| 8,172,798 B2 | 5/2012 | Hungerford et al. |
| 8,185,322 B2 | 5/2012 | Schroeder et al. |
| 8,195,478 B2 | 6/2012 | Petersen |
| 8,206,350 B2 | 6/2012 | Mann et al. |
| 8,219,413 B2 | 7/2012 | Martinez et al. |
| 8,231,578 B2 | 7/2012 | Fathallah et al. |
| 8,234,128 B2 | 7/2012 | Martucci et al. |
| 8,267,892 B2 | 9/2012 | Spencer et al. |
| 8,271,106 B2 | 9/2012 | Wehba et al. |
| 8,287,495 B2 | 10/2012 | Michaud et al. |
| 8,291,337 B2 | 10/2012 | Gannin et al. |
| 8,298,184 B2 | 10/2012 | DiPerna et al. |
| 8,352,290 B2 | 1/2013 | Bartz et al. |
| 8,359,338 B2 | 1/2013 | Butterfield et al. |
| 8,380,536 B2 | 2/2013 | Howard et al. |
| 8,387,112 B1 | 2/2013 | Ranjan et al. |
| 8,394,077 B2 | 3/2013 | Jacobson et al. |
| 8,403,908 B2 | 3/2013 | Jacobson et al. |
| 8,435,206 B2 | 5/2013 | Evans et al. |
| 8,449,523 B2 | 5/2013 | Brukalo et al. |
| 8,452,953 B2 | 5/2013 | Buck et al. |
| 8,453,645 B2 | 6/2013 | Figueiredo et al. |
| 8,480,648 B2 | 7/2013 | Burnett et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,543,416 B2 | 9/2013 | Palmroos et al. |
| 8,551,038 B2 | 10/2013 | Tsoukalis et al. |
| 8,560,345 B2 | 10/2013 | Wehba et al. |
| 8,577,692 B2 | 11/2013 | Silkaitis et al. |
| 8,579,884 B2 | 11/2013 | Lanier et al. |
| 8,655,676 B2 | 2/2014 | Wehba et al. |
| 8,660,860 B2 | 2/2014 | Wehba et al. |
| 8,662,388 B2 | 3/2014 | Belkin |
| 8,666,769 B2 | 3/2014 | Butler et al. |
| 8,700,421 B2 | 4/2014 | Feng et al. |
| 8,731,960 B2 | 5/2014 | Butler et al. |
| 8,768,719 B2 | 7/2014 | Wehba et al. |
| 8,771,251 B2 | 7/2014 | Ruchti et al. |
| 8,777,894 B2 | 7/2014 | Butterfield et al. |
| 8,777,895 B2 | 7/2014 | Hsu et al. |
| 8,799,012 B2 | 8/2014 | Butler et al. |
| 8,876,793 B2 | 11/2014 | Ledford et al. |
| 8,922,330 B2 | 12/2014 | Moberg et al. |
| 8,936,565 B2 | 1/2015 | Chawla |
| 8,952,794 B2 | 2/2015 | Bloomquist et al. |
| 8,998,100 B2 | 4/2015 | Halbert et al. |
| 9,026,370 B2 | 5/2015 | Rubalcaba et al. |
| 9,069,887 B2 | 6/2015 | Gupta et al. |
| 9,089,642 B2 | 7/2015 | Murphy et al. |
| 9,114,217 B2 | 8/2015 | Sur et al. |
| 9,123,077 B2 | 9/2015 | Silkaitis et al. |
| 9,192,712 B2 | 11/2015 | DeBelser et al. |
| 9,240,002 B2 | 1/2016 | Hume et al. |
| 9,381,296 B2 | 7/2016 | Arrizza et al. |
| 9,393,362 B2 | 7/2016 | Cozmi et al. |
| 9,498,583 B2 | 11/2016 | Sur et al. |
| 9,539,383 B2 | 1/2017 | Kohlbrecher |
| 9,572,923 B2 | 2/2017 | Howard et al. |
| 9,594,875 B2 | 3/2017 | Arrizza et al. |
| 9,604,000 B2 | 3/2017 | Wehba et al. |
| 9,641,432 B2 | 5/2017 | Jha et al. |
| 9,649,431 B2 | 5/2017 | Gray et al. |
| 9,662,436 B2 | 5/2017 | Belkin et al. |
| 9,690,909 B2 | 6/2017 | Stewart et al. |
| 9,707,341 B2 | 7/2017 | Dumas, III et al. |
| 9,724,470 B2 | 8/2017 | Day et al. |
| 9,764,082 B2 | 9/2017 | Day et al. |
| 9,971,871 B2 | 5/2018 | Arrizza et al. |
| 9,995,611 B2 | 6/2018 | Ruchti et al. |
| 10,022,498 B2 | 7/2018 | Ruchti et al. |
| 10,042,986 B2 | 8/2018 | Ruchti et al. |
| 10,046,112 B2 | 8/2018 | Oruklu et al. |
| 2001/0016056 A1 | 8/2001 | Westphal et al. |
| 2001/0031944 A1 | 10/2001 | Peterson et al. |
| 2001/0032099 A1 | 10/2001 | Joao |
| 2001/0037060 A1 | 11/2001 | Thompson et al. |
| 2001/0044731 A1 | 11/2001 | Coffman et al. |
| 2001/0051787 A1 | 12/2001 | Haller et al. |

(56) References Cited

U.S. PATENT DOCUMENTS

| | | |
|---|---|---|
| 2001/0056358 A1 | 12/2001 | Dulong et al. |
| 2002/0010595 A1 | 1/2002 | Kapp |
| 2002/0013723 A1 | 1/2002 | Mise |
| 2002/0015018 A1 | 2/2002 | Shimazu et al. |
| 2002/0019584 A1 | 2/2002 | Schulze et al. |
| 2002/0026103 A1 | 2/2002 | Norris et al. |
| 2002/0029776 A1 | 3/2002 | Blomquist |
| 2002/0032583 A1 | 3/2002 | Joao |
| 2002/0040208 A1 | 4/2002 | Flaherty et al. |
| 2002/0040282 A1 | 4/2002 | Bailey et al. |
| 2002/0077852 A1 | 6/2002 | Ford et al. |
| 2002/0082728 A1 | 6/2002 | Mueller et al. |
| 2002/0087115 A1 | 7/2002 | Hartlaub |
| 2002/0087116 A1 | 7/2002 | Hartlaub |
| 2002/0095486 A1 | 7/2002 | Bahl |
| 2002/0103675 A1 | 8/2002 | Vanelli |
| 2002/0123905 A1 | 9/2002 | Goodroe et al. |
| 2002/0152239 A1 | 10/2002 | Bautista-Lloyd et al. |
| 2002/0169636 A1 | 11/2002 | Eggers et al. |
| 2002/0194329 A1 | 12/2002 | Ailing |
| 2003/0009244 A1 | 1/2003 | Engleson |
| 2003/0013959 A1 | 1/2003 | Grunwald et al. |
| 2003/0014222 A1 | 1/2003 | Klass et al. |
| 2003/0014817 A1 | 1/2003 | Gallant et al. |
| 2003/0025602 A1 | 2/2003 | Medema et al. |
| 2003/0028082 A1 | 2/2003 | Thompson |
| 2003/0036683 A1 | 2/2003 | Kehr et al. |
| 2003/0047126 A1 | 3/2003 | Tomaschko |
| 2003/0050621 A1 | 3/2003 | Lebel et al. |
| 2003/0059750 A1 | 3/2003 | Bindler et al. |
| 2003/0060688 A1 | 3/2003 | Ciarniello et al. |
| 2003/0069963 A1 | 4/2003 | Jayant et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0106553 A1 | 6/2003 | Vanderveen |
| 2003/0114836 A1 | 6/2003 | Estes et al. |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1* | 10/2003 | Peebles ............... G06F 11/0709 714/25 |
| 2003/0212364 A1 | 11/2003 | Mann et al. |
| 2003/0212379 A1 | 11/2003 | Bylund et al. |
| 2003/0217962 A1 | 11/2003 | Childers et al. |
| 2004/0015132 A1 | 1/2004 | Brown |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |
| 2005/0086072 A1 | 4/2005 | Fox |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102669 A1 | 5/2005 | Marney et al. |
| 2005/0107923 A1 | 5/2005 | Vanderveen |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0137522 A1 | 6/2005 | Aoki |
| 2005/0137573 A1 | 6/2005 | McLaughlin |
| 2005/0137653 A1 | 6/2005 | Friedman et al. |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox, Jr. et al. |
| 2005/0273059 A1 | 12/2005 | Mernoe et al. |
| 2005/0277873 A1 | 12/2005 | Stewart et al. |
| 2005/0277890 A1 | 12/2005 | Stewart et al. |

(56) References Cited

U.S. PATENT DOCUMENTS

| | | |
|---|---|---|
| 2005/0277911 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229551 A1 | 10/2006 | Martinez et al. |
| 2006/0229557 A1 | 10/2006 | Fathallah et al. |
| 2006/0229918 A1 | 10/2006 | Fotsch et al. |
| 2006/0258985 A1 | 11/2006 | Russell |
| 2006/0259327 A1 | 11/2006 | Hoag |
| 2006/0264895 A1 | 11/2006 | Flanders |
| 2006/0265186 A1 | 11/2006 | Holland et al. |
| 2006/0265246 A1 | 11/2006 | Hoag |
| 2006/0267753 A1 | 11/2006 | Hussey et al. |
| 2006/0268710 A1 | 11/2006 | Appanna et al. |
| 2006/0277206 A1* | 12/2006 | Bailey .................. G06F 11/328 707/999.102 |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0065363 A1 | 3/2007 | Dalal et al. |
| 2007/0073419 A1 | 3/2007 | Sesay |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213657 A1 | 9/2007 | Jennewine et al. |
| 2007/0214003 A1 | 9/2007 | Holland et al. |
| 2007/0215545 A1 | 9/2007 | Bissler et al. |
| 2007/0229249 A1 | 10/2007 | McNeal et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0126969 A1 | 5/2008 | Blomquist |
| 2008/0139907 A1 | 6/2008 | Rao et al. |
| 2008/0149117 A1 | 6/2008 | Raghuram |
| 2008/0154177 A1* | 6/2008 | Moubayed .......... G06F 19/3468 604/19 |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0200870 A1 | 8/2008 | Palmroos et al. |
| 2008/0214919 A1 | 9/2008 | Harmon et al. |
| 2008/0243055 A1 | 10/2008 | Fathallah et al. |
| 2008/0246748 A1 | 10/2008 | Cassidy et al. |
| 2008/0256305 A1 | 10/2008 | Kwon |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0320387 A1 | 12/2008 | Sasaki et al. |
| 2008/0320466 A1 | 12/2008 | Dias |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0069785 A1 | 3/2009 | Miller et al. |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0156991 A1 | 6/2009 | Roberts |
| 2009/0157695 A1 | 6/2009 | Roberts |
| 2009/0158274 A1 | 6/2009 | Roberts |
| 2009/0177146 A1 | 7/2009 | Nesbitt et al. |
| 2009/0177769 A1* | 7/2009 | Roberts .................. G06F 19/327 709/224 |
| 2009/0177992 A1 | 7/2009 | Rubalcaba et al. |
| 2009/0183147 A1 | 7/2009 | Davis et al. |
| 2009/0209938 A1 | 8/2009 | Aalto-Setala |

(56) References Cited

U.S. PATENT DOCUMENTS

| | | |
|---|---|---|
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Bloomquist et al. |
| 2009/0275896 A1 | 11/2009 | Kamen et al. |
| 2009/0284691 A1 | 11/2009 | Marhefka et al. |
| 2009/0326340 A1 | 12/2009 | Wang |
| 2009/0326516 A1 | 12/2009 | Bangers et al. |
| 2010/0022988 A1 | 1/2010 | Wochner |
| 2010/0036310 A1 | 2/2010 | Hillman |
| 2010/0056992 A1 | 3/2010 | Hayter |
| 2010/0095229 A1 | 4/2010 | Dixon et al. |
| 2010/0121170 A1 | 5/2010 | Rule |
| 2010/0121415 A1 | 5/2010 | Skelton et al. |
| 2010/0121654 A1 | 5/2010 | Portnoy et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0204574 A1 | 8/2010 | Duchon et al. |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1* | 9/2010 | Bucknell ............ H04L 41/5038 709/224 |
| 2010/0271479 A1 | 10/2010 | Heydlauf |
| 2010/0273738 A1 | 10/2010 | Valcke et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0001605 A1 | 1/2011 | Kiani et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0125095 A1 | 5/2011 | Lebel et al. |
| 2011/0175728 A1 | 7/2011 | Baker, Jr. |
| 2011/0178462 A1* | 7/2011 | Moberg ............... A61B 5/0002 604/151 |
| 2011/0231216 A1 | 9/2011 | Fyke et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0011253 A1* | 1/2012 | Friedman ............ A61B 5/0002 709/224 |
| 2012/0016305 A1 | 1/2012 | Jollota |
| 2012/0029941 A1 | 2/2012 | Malave et al. |
| 2012/0070045 A1 | 3/2012 | Vesper et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0130308 A1 | 5/2012 | Silkaitis et al. |
| 2012/0143116 A1 | 6/2012 | Ware et al. |
| 2012/0150556 A1 | 6/2012 | Galasso et al. |
| 2012/0172802 A1 | 7/2012 | Blomquist |
| 2012/0179135 A1 | 7/2012 | Rinehart et al. |
| 2012/0179136 A1 | 7/2012 | Rinehart et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0277716 A1 | 11/2012 | Ali et al. |
| 2012/0284734 A1 | 11/2012 | McQuaid et al. |
| 2012/0323212 A1 | 12/2012 | Murphy |
| 2013/0006666 A1 | 1/2013 | Schneider |
| 2013/0006702 A1 | 1/2013 | Wu |
| 2013/0012880 A1 | 1/2013 | Blomquist |
| 2013/0015980 A1 | 1/2013 | Evans et al. |
| 2013/0036403 A1 | 2/2013 | Geist |
| 2013/0036412 A1 | 2/2013 | Birtwhistle et al. |
| 2013/0066265 A1 | 3/2013 | Grant |
| 2013/0072872 A1 | 3/2013 | Yodfat et al. |
| 2013/0085689 A1 | 4/2013 | Sur et al. |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0138452 A1 | 5/2013 | Cork et al. |
| 2013/0144206 A1 | 6/2013 | Lee et al. |
| 2013/0158504 A1 | 6/2013 | Ruchti et al. |
| 2013/0167245 A1 | 6/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0261993 A1 | 10/2013 | Ruchti et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2014/0039446 A1 | 2/2014 | Day |
| 2014/0257251 A1 | 9/2014 | Bush et al. |
| 2014/0266790 A1* | 9/2014 | Al-Ali .................. G08C 17/02 340/870.09 |
| 2014/0269643 A1 | 9/2014 | Sun |
| 2014/0350513 A1 | 11/2014 | Oruklu et al. |
| 2014/0358077 A1 | 12/2014 | Oruklu et al. |
| 2014/0366878 A1 | 12/2014 | Baron |
| 2015/0005935 A1 | 1/2015 | Bae et al. |
| 2015/0058044 A1 | 2/2015 | Butler et al. |
| 2015/0066531 A1 | 3/2015 | Jacobson et al. |
| 2015/0100038 A1 | 4/2015 | McCann et al. |
| 2015/0141955 A1 | 5/2015 | Ruchti et al. |
| 2015/0151051 A1 | 6/2015 | Tsoukalis |
| 2015/0317891 A1 | 11/2015 | Day et al. |
| 2015/0379237 A1 | 12/2015 | Mills et al. |
| 2016/0051749 A1 | 2/2016 | Istoc |
| 2016/0051751 A1 | 2/2016 | Silkaitis et al. |
| 2016/0103960 A1 | 4/2016 | Hume et al. |
| 2016/0228633 A1 | 8/2016 | Welsch et al. |
| 2016/0350513 A1 | 12/2016 | Jacobson et al. |
| 2017/0024534 A1 | 1/2017 | Arrizza et al. |
| 2017/0246388 A1 | 8/2017 | Kohlbrecher |
| 2017/0274140 A1 | 9/2017 | Howard et al. |
| 2017/0286637 A1 | 10/2017 | Arrizza et al. |
| 2017/0319780 A1 | 11/2017 | Belkin et al. |
| 2017/0331735 A1 | 11/2017 | Jha et al. |
| 2018/0008772 A1 | 1/2018 | Wehba et al. |
| 2018/0028742 A1 | 2/2018 | Day et al. |
| 2018/0043094 A1 | 2/2018 | Day et al. |

FOREIGN PATENT DOCUMENTS

| | | |
|---|---|---|
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |

(56) References Cited

FOREIGN PATENT DOCUMENTS

| | | |
|---|---|---|
| EP | 0 384 155 | 8/1990 |
| EP | 0 460 533 | 12/1991 |
| EP | 0 564 127 | 6/1993 |
| EP | 0 633 035 | 1/1995 |
| EP | 0 652 528 | 5/1995 |
| EP | 0 672 427 | 9/1995 |
| EP | 0 683 465 | 11/1995 |
| EP | 0 880 936 | 12/1998 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| FR | 2 717 919 | 9/1995 |
| GB | 2 285 135 | 6/1995 |
| JP | 04-161139 | 6/1992 |
| JP | H07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-518479 | 7/2007 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2012-070991 | 4/2012 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | WO 96/008755 | 3/1996 |
| WO | WO 96/025186 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/050526 | 6/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/057729 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |
| WO | WO 2017/176928 | 10/2017 |

OTHER PUBLICATIONS

Gabel, M. & Haungs, M. Camp: a common API for measuring performance. In Large Installation System Administration Conference 49-62 (Usenix, 2007).*

Akridge, Jeannie, "New Pumps Outsmart User Error", Healthcare Purchasing News, Apr. 2011, pp. 10, http://web.archive.org/web/20110426122450/http://www.hpnonline.com/inside/2011-04/1104-OR-Pumps.html.

Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.

ASHP Advantage, "Improving Medication Safety in Health Systems Throught Innovations in Automation Technology", Proceedings of Educational Symposium and Educational Sessions during the 39th ASHP Midyear Clinical Meeting, Dec. 5-9, 2004, Orlando, FL, pp. 28.

Bektas et al., "Bluetooth Communication Employing Antenna Diversity", Proceedings of Eight IEEE International Symposium on Computers and Communication, Jul. 2003, pp. 6.

Braun, "Infusomat® Space and Accessories", Instructions for Use, Nov. 2010, pp. 68. http://corp.bbraun.ee/Extranet/infusioonipumbad/Kasutusjuhendid/Vanad/Kasutusjuhend-Infusomat_Space (vers688J,inglise_k.pdf.

Brownlee, Seth, "Product Spotlight: The Plum A+ with Hospira MedNet Infusion System", PP&P Magazine, Dec. 2005, vol. 2, No. 7, pp. 2.

Cannon, MD et al., "Automated Heparin-Delivery System to Control Activated Partial Thromboplastin Time", Circulation, Feb. 16, 1999, vol. 99, pp. 751-756.

(56) References Cited

OTHER PUBLICATIONS

Cardinal Health, "Alaris® Syringe Pumps" Technical Service Manual, Copyright 2002-2006, Issue 9, pp. 1-88, http://www.frankshospitalworkshop.com/equipment/documents/infusion_pumps/service_manuals/Cardinal_Alaris_-_Service_Manual.pdf
"CareAware® Infusion Management", Cerner Store, as printed May 12, 2011, pp. 3, https://store.cerner.com/items/7.
Chen et al., "Enabling Location-Based Services on Wireless LANs", The 11th IEEE International Conference on Networks, ICON 2003, Sep. 28-Oct. 1, 2003, pp. 567-572.
"Computer Dictionary", Microsoft Press, Third Edition, Microsoft Press, 1997, pp. 430 & 506.
Crocker et al., "Augmented BNF for Syntax Specifications: ABNF", Network Working Group, Standards Track, Jan. 2008, pp. 16.
Einhorn, George W., "Total Quality Pain Management: A Computerized Quality Assessment Tool for Postoperative Pain Management", Abbott Laboratories, Chicago, IL, Mar. 2, 2000, pp. 1-4.
Eskew et al., "Using Innovative Technologies to Set New Safety Standards for the Infusion of Intravenous Medications", Hospital Pharmacy, 2002, vol. 37, No. 11, pp. 1179-1189.
Galt et al., "Personal Digital Assistant-Based Drug Information Sources: Potential to Improve Medication Safety", Journal of Medical Library Association, Apr. 2005, vol. 93, No. 2, pp. 229-236.
"General-Purpose Infusion Pumps", Health Devices, EXRI Institute, Oct. 1, 2002, vol. 31, No. 10, pp. 353-387.
Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.
Gomez et al., "CLAM: Connection-Less, Lightweight, and Multiway Communication Support for Distributed Computing", Computer Science, 1997, vol. 1199, pp. 227-240.
Graseby, "Model 3000/500 and Micro 3100/505: Volumetric Infusion Pump", Technical Service Manual, Graseby Medical Ltd., Apr. 2002, Issue A, pp. 160.
Graseby, "Model 3000/500 and Micro 3100/505: Volumetric Infusion Pump: Illustrated Parts List for Pump Serial Nos. from 3000 to 59,999", Technical Service Manual, Graseby Medical Ltd., Apr. 2002, Issue A, pp. 71.
Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.
Introducing Abbott TQPM (Total Quality Pain Management), Abbott Laboratories, Abbott Park, IL, May 2000, pp. 1-4.
Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
Medfusion™, "Medfusion Syringe Infusion Pump Model 4000", Operator's Manual, Software Version V1.1, Sep. 2011, pp. 154. http://www.medfusionpump.com/assets/literature/manuals/Operators_Manual_4000_40-5760-51A.pdf.
Micrel Medical Devices, "MP Daily +" http://web.archive.org/web/20130803235715/http://www.micrelmed.com/index.aspx?productid=9 as archived Aug. 3, 2013 in 1 page.
O'Shea, Kristen L., "Infusion Management: Working Smarter, Not Harder", Hospital Pharmacy, Apr. 2013, vol. 48, No. 3, pp. S1-S14.
Passos et al., "Distributed Software Platform for Automation and Control of General Anaesthesia", Eighth International Symposium on Parallel and Distributed Computing, ISPDC '09, Jun. 30-Jul. 4, 2009, pp. 8.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
"Sigma Spectrum: Operator's Manual", Oct. 2009, pp. 72. http://static.medonecapital.com/manuals/userManuals/Sigma-Spectrum-Operator-Manual-October-2009.pdf.

Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. http://www.thomasland.com/hpl4209-832.pdf.
Smith, Joe, "Infusion Pump Informatics", CatalyzeCare: Transforming Healthcare, as printed May 12, 2011, pp. 2.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.
Van Der Maas et al., "Requirements for Medical Modeling Languages", Journal of the American Medical Informatics Association, Mar./Apr. 2001, vol. 8, No. 2, pp. 146-162.
Wilkins et al., "A Regular Language: The Annotated Case Report Form", PPD Inc., PharmaSUG2011—Paper CD18, 2011, pp. 1-9.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
Beard et al., "Total Quality Pain Management: History, Background, Resources", Abbott Laboratories, TQPM Survey History, available Feb. 2015 or earlier, pp. 1-3.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Crawford, Anne J., MSN, RNC, "Building a Successful Quality Pain Service: Using Patient Satisfaction Data and the Clinical Practice Guideline", USA, 1995, pp. 1-6.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Davies, T., "Cordless Data Acquisition in a Hospital Environment", IEE Colloquium on Cordless Computing—Systems and User Experience, 1993, pp. 4.
Dayhoff et al., "Medical Data Capture and Display: The Importance of Clinicians' Workstation Design", AMIA, Inc., 1994, pp. 541-545.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
East PhD et al., "Digital Electronic Communication Between ICU Ventilators and Computers and Printers", Respiratory Care, Sep. 1992, vol. 37, No. 9, pp. 1113-1122.
Philips, "IntelliSpace Event Management and IntelliVue Patient Monitoring", Release 10, 2011, http://incenter.medical.philips.com/doclib/enc/fetch/2000/4504/577242/577243/577247/582646/583147/8359175/Philips_Patient_Monitoring_and_IntelliSpace_Event_Management_Interoperablity.pdf%3fnodeid%3d8508574%26verrium%3d-2, pp. 2.
Felleiter et al., "Data Processing in Prehospital Emergency Medicine", International journal of Clinical Monitoring and Computing, Feb. 1995, vol. 12, No. 1, pp. 37-41.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Gage et al., "Automated Anesthesia Surgery Medical Record System", International Journal of Clinical Monitoring and Computing, Dec. 1990, vol. 7, No. 4, pp. 259-263.
Gardner, Ph.D. et al., "Real Time Data Acquisition: Recommendations for the Medical Information Bus (MIB)", 1992, pp. 813-817.

(56) References Cited

OTHER PUBLICATIONS

Glaeser, "A Hierarchical Minicomputer System for Continuous Post-Surgical Monitoring", Computers and Biomedical Research, Aug. 31, 1975, pp. 336-361.
Goldberg et al., "Clinical Results of an Updated Insulin Infusion Protocol in Critically Ill Patients", Diabetes Spectrum, 2005, vol. 18, No. 3, pp. 188-191.
"GPS Tracker for Medical Equipment" http://www.trackingsystem.com/forouslnesses/corporate-trackingsystem/1098-gps-tracker-formedicalequipment.html, Mar. 15, 2015, pp. 2.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hasegawa et al., "On a Portable Memory Device for Physical Activities and Informations of Maternal Perception", Journal of Perinatal Medicine, 1988, vol. 16, No. 4, pp. 349-356.
Hawley et al., "Clinical Implementation of an Automated Medical Information Bus in an Intensive Care Unit", Proceedings of the Annual Symposium on Computer Application in Medical Care, Nov. 9, 1988, pp. 621-624.
Hayes-Roth et al., "Guardian: A Prototype Intelligent Agent for Intensive-Care Monitoring", Artificial Intelligence in Medicine, vol. 4, Dec. 31, 1992, pp. 165-185.
Hospira, Gemstar® Pain Management Infusion System 9-084-PR1-2-2, www.hospira.com/products/gemstar_painmanagement.aspx Jan. 28, 2010, pp. 1-2.
Isaka et al. "Control Strategies for Arterial Blood Pressure Regulation", IEEE Transactions on Biomedical Engineering, Apr. 1993, vol. 40, No. 4, pp. 353-363.
Johnson et al., "Using BCMA Software to Improve Patient Safety in Veterans Administration Medical Centers", Journal of Healthcare Information Management, Dec. 6, 2004, vol. 16, No. 1, pp. 46-51.
Kent Displays, "Reflex™ Electronic Skins", Product Brief 25127B, 2009, pp. 2.
Kent Displays, "Reflex Electronic Skins Engineering Evaluation Kit", 25136A, Mar. 10, 2009.
Lefkowitz et al., "A Trial of the Use of Bar Code Technology to Restructure a Drug Distribution and Administration System", Hospital Pharmacy, Mar. 31, 1991, vol. 26, No. 3, pp. 239-242.
Lenssen et al., "Bright Color Electronic Paper Technology and Applications", IDS '09 Publication EP1-2 (Phillips Research), 2009, pp. 529-532.
Leveson, Nancy, "Medical Devices: The Therac-25", Appendix A, University of Washington, 1995, pp. 49.
Linkens, D.A. "Computer Control for Patient Care", Computer Control of Real-Time Processes, IEE Control Engineering Series 41, 1990, Ch. 13, pp. 216-238.
Mako Hill et al., "The Official Ubuntu Book", Shoeisha Co., Ltd., 1st Edition, Jun. 11, 2007, pp. 115 to 125.
Marshall, et al., "New Microprocessor-Based Insulin Controller", IEEE Transactions on Biomedical Engineering, Nov. 1983, vol. BME-30, No. 11, pp. 689-695.
Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.
Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.
Moghissi, Etie, MD, FACP, FACE, "Hyperglycemia in Hospitalized Patients", A Supplement to ACP Hospitalist, Jun. 15, 2008, pp. 32.
Murray, Jr. et al., "Automated Drug Identification System (during surgery)", IEEE Proceedings of Southeastcon '91, Apr. 7-10, 1991, pp. 265.
Nicholson et al., "'Smart' Infusion Apparatus for Computation and Automated Delivery of Loading, Tapering, and Maintenance Infusion Regimens of Lidocaine, Procainamide, and Theophylline", Proceedings of the Seventh Annual Symposium on Computer Applications in Medical Care, Oct. 1983, pp. 212-213.
Nolan et al., "The P1073 Medical Information Bus Standard: Overview and Benefits for Clinical Users", 1990, pp. 216-219.
Omnilink Systems, Inc., "Portable Medical Equipment Tracking", http://www.omnilink.com/portablemedicalequipmenttracking/, Mar. 15, 2015, pp. 2.
Package Management in Debian GNU/Linux, Debian GNU/Linux Expert Desktop Use Special, Giutsu-Hyohron Co., Ltd., First Edition, Sep. 25, 2004, pp. 183-185.
Rappoport, Arthur E., "A Hospital Patient and Laboratory machine—Readable Identification System (MRIS) Revisited", Journal of Medical Systems, Apr. 1984, vol. 8, Nos. 1/2, pp. 133-156.
Ritchie et al., "A Microcomputer Based Controller for Neuromuscular Block During Surgery", Annals of Biomedical Engineering, Jan. 1985, vol. 13, No. 1, pp. 3-15.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sanders et al., "The Computer in a Programmable Implantable Medication System (PIMS)", Proceedings of the Annual Symposium on Computer Application in Medical Care, Nov. 2, 1982, pp. 682-685.
Schilling et al., "Optimizing Outcomes! Error Prevention and Evidence-Based Practice with IV Medications", A Pro-Ce Publication, Hospira, Inc., Feb. 6, 2012, pp. 56.
Schulze et al., "Advanced Sensors Technology Survey", Final Report, Feb. 10, 1992, pp. 161.
Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D. "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Slack, W.V., "Information Technologies for Transforming Health Care", https://www.andrew.cmu.edu/course/90-853/medis.dir/otadocs.dir/03ch2.pdf, Ch. 2, 1995, pp. 29-78.
Sodder, Lisa, "A Center Keeps Medicine in Right Hands", Dec. 4, 1999, pp. 1-2.
Stitt, F.W., "The Problem-Oriented Medical Synopsis: a Patient-Centered Clinical Information System", Proceedings of the Annual Symposium on Computer Application in Medical Care, 1994, pp. 88-92.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.

(56) References Cited

OTHER PUBLICATIONS

Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.

Van Den Berghe, M.D., Ph.D., et al., "Intensive Insulin Therapy in the Medical ICU", The New England Journal of Medicine, Feb. 2, 2006, vol. 354, No. 5, pp. 449-461.

Villalobos et al., "Computerized System in Intensive Care medicine", Medical Informatics, vol. 11, No. 3, 1986, pp. 269-275.

Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.

Yurkonis et al., "Computer Simulation of Adaptive Drug Infusion", IEEE Transactions on Biomedical Engineering, vol. BME-34, No. 8, Aug. 1987, pp. 633-635.

"Infusion Pump", Wikipedia.org, https://web.archive.org/web/20140703024932/https://en.wikipedia.org/wiki/Infusion_pump, as last modified Mar. 27, 2014, pp. 3.

Sutton et al., "The Syntax and Semantics of the PROforma Guideline Modeling Language", Journal of the American Medical Informatics Association, Sep./Oct. 2003, vol. 10, No. 5, pp. 433-443.

\* cited by examiner $$\begin{aligned}
\text{MaxIndexNumber} &= \left(\frac{(\text{HmssMaxCPU\%} + \text{HmssAvgCPU\%})}{2} * \text{HmssCPU\%}\right) + \left(\frac{(\text{SqlMaxCPU\%} + \text{SqlAvgCPU\%})}{2} * \text{SqlCPU\%}\right) + f(x) \\
&* \frac{\text{NumOfJMSMsg}}{\text{NumOfInfusers} * 10} * \text{NumOfJMSMsg\%}, \quad f(x) = \begin{cases} \frac{\text{NumOfJMSMsg}}{\text{NumOfInfusers} * 10}, & \text{NumOfJMSMsg} < \text{NumOfInfusers} * 10 \\ \text{NumOfJMSMsg\%}, & \text{Otherwise} \end{cases} \\
&+ \left(f(x) = \begin{cases} \frac{\text{AvgHmssPQL}}{\text{NumHmssCore} * 1.5}, & \text{AvgHmssPQL} < \text{NumHmssCore} * 1.5 \\ 1, & \text{Otherwise} \end{cases}\right) * f(x) = \begin{cases} \frac{\text{HmssPQL\%}}{(\text{HmssPQL\%} + \text{SqlPQL\%})}, & \text{Svr Cfg} = \text{Distributed} \\ \text{HmssPQL\%}, & \text{Otherwise} \end{cases} + f(x) \\
&+ \left(f(x) = \begin{cases} \frac{\text{HmssDQL}}{1.75}, & \text{HmssDQL} \leq 2 \\ 1, & \text{Otherwise} \end{cases}\right) * f(x) = \begin{cases} \frac{\text{HmssDQL\%}}{(\text{HmssDQL\%} + \text{SqlDQL\%})}, & \text{Svr Cfg} = \text{Distributed} \\ \text{HmssDQL\%}, & \text{Otherwise} \end{cases} \\
&= \begin{cases} \frac{\text{SqlDQL}}{1.75} * \text{SqlDQL\%}, & \text{SQLDQL} \leq 2 \\ \text{SqlDQL\%}, & \text{Otherwise} \end{cases} + f(x) = \begin{cases} \frac{\text{AvgSQLPQL}}{\text{NumSQLCore} * 1.5} * \text{HmssPQL\%}, & \text{AvgSqlPQL} < \text{NumSQLCore} * 1.5 \\ \text{HmssPQL\%}, & \text{Otherwise} \\ 0, & \text{Svr Cfg} = \text{Distributed} \end{cases} \\
&+ \left(\frac{\text{MemUsed}}{\text{MaxMem}}\right) * \text{MemUsage\%}
\end{aligned}$$

| Phases | Vanilla Symbiq | Vanilla Symbiq w/ IVCI |
|---|---|---|
| 5.5 Baseline | 74.037 | N/A |
| Phase 1 | 71.067 | 70.285 |
| Phase 2 | 66.476 | 71.847 |
| Phase 3 | 46.344 | 52.424 |
| Phase 4 | 51.490 | 53.667 |
| Phase 5 (5.81.002) | N/A | 57.473 |
| Customer X | N/A | 5.954 |

MEDICAL DEVICE SYSTEM PERFORMANCE INDEX

BACKGROUND OF THE INVENTION

As technology becomes increasingly computer-based, medical devices are more commonly utilizing electronic features that interact with a larger system. For example, a hospital information system can transfer data to and from a medication management unit, which can facilitate communication with a plurality of specific hospital beds or medical devices to record and transmit treatment parameters for patients. In another example, medical devices can be programmed to notify clinicians when certain alarms or occurrences of a particular event are triggered. Furthermore, medical facilities routinely utilize electronic databases such as drug libraries and bar code systems to improve the administration of medication and prevent human errors. Thus, an electronic network system can be quite extensive and complex in a typical hospital setting due to the interaction of the various system components.

Infusion pumps are one type of medical device and are used for intravenous delivery of medicines such as insulin, analgesics, sedatives, vasopressors, heparin and anti-arrhythmics to patients. Correct delivery of these medications is important for avoiding adverse events, particularly in critically ill patients. Smart infusion pumps, which include drug libraries and integrated decision support software in their medication delivery systems, have decreased errors in administration of medications by incorporating features such as hard and soft alarm limits, clinician messaging, and medication barcode input. Smart pumps are also able to utilize electronic medical records and inputs customizable for specific clinical care areas, wards or to improve safety for individual patients. Other infusion systems have incorporated features for a specific disease, such as algorithms to change the rates of insulin delivery based on a patient's glucose level, or to offer procedures specifically for advanced cardiac life support.

SUMMARY OF THE INVENTION

A distributed network system and method includes a processing unit configured to manage safety data for a plurality of medical devices, a database software component in communication with the processing unit, and a monitoring software component in communication with the processing unit. The monitoring software component is configured to monitor a number of messages between a number of medical devices and the processing unit, to process performance parameters to generate an overall performance index, and to generate an output that is viewable by a user. The output includes relative contributions of each of the performance parameters to the overall performance index, where the overall performance index is generated using a weighting factor associated with each of the performance parameters. The performance parameters include the number of messages waiting to be processed, which has the largest weighting factor, and a disk queue length, which has the smallest weighting factor.

BRIEF DESCRIPTION OF THE DRAWINGS

Each of the aspects and embodiments of the invention described herein can be used alone or in combination with one another. The aspects and embodiments will now be described with reference to the attached drawings.

FIG. 6 shows an equation for calculating a performance index, in one embodiment;

DETAILED DESCRIPTION OF THE EMBODIMENTS

Figure 1:
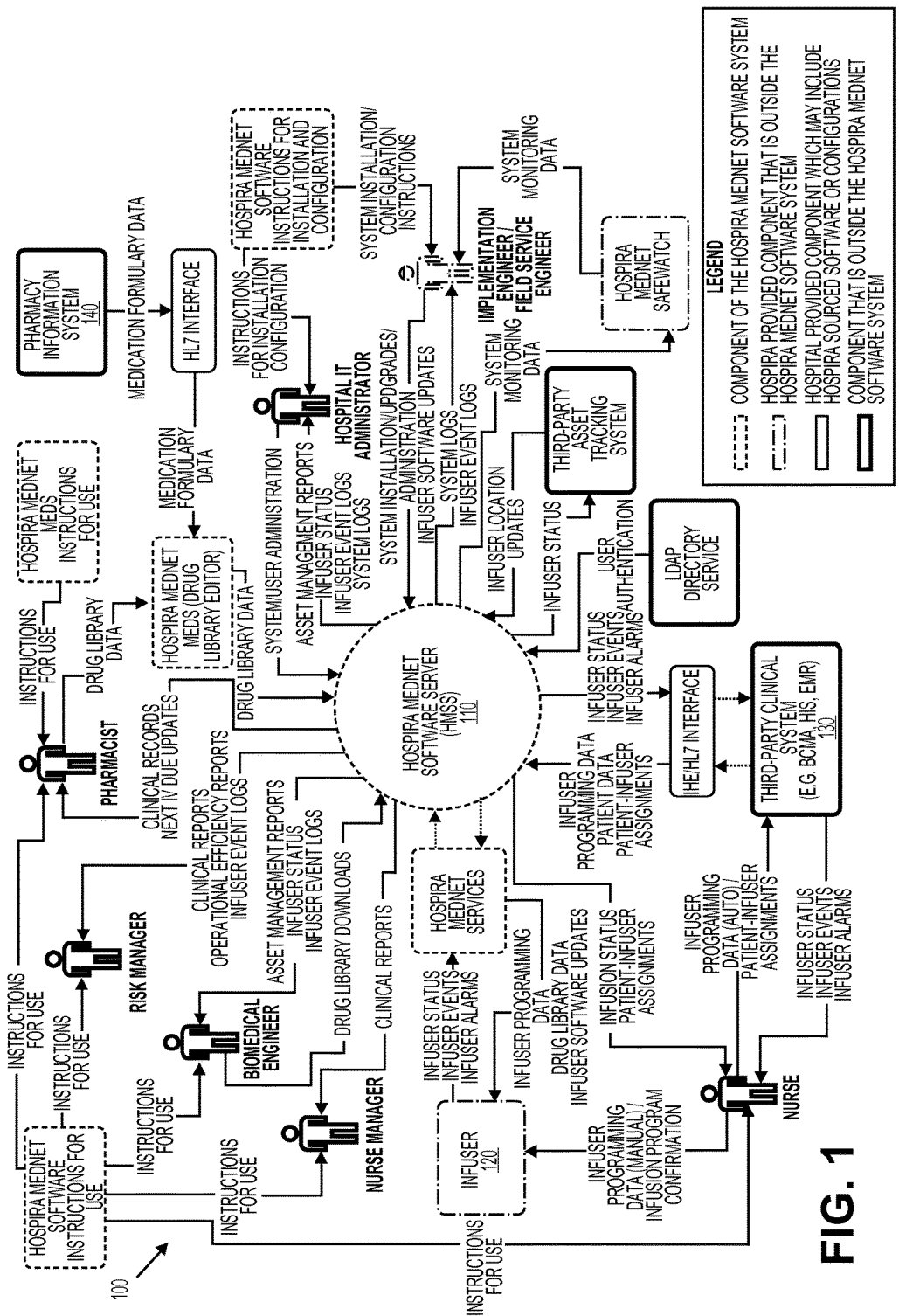
FIG. 1 shows a system context diagram of an exemplary medical device network system.

FIG. 1 provides a system context diagram of an exemplary medical device network system 100. The system 100 includes a medical device management component 110 that is configured to manage safety data for a plurality of medical devices. In this figure, the management component 110 is shown as Hospira MedNet™ Software, manufactured and sold by Hospira, Inc., the assignee of the present disclosure. However, other medical device management systems may be utilized instead. Similarly, the medical devices described herein shall be referred to as infusers or infusion pumps; however, other types of medical equipment with electronic data interfaces such as hospital beds, patient monitoring units, or surgical devices are applicable.

In FIG. 1, the medical device management component 110 has a software server (Hospira MedNet™ Software Server "HMSS") that interfaces to a medical device such as an infuser 120, and also provides communication with other systems such as a third-party clinical system 130 and a pharmacy information system 140. Third-party clinical system 130 may be, for example, a bar code medication administration (BCMA), hospital information system (HIS), or electronic medical record (EMR). Thus, the medical device management component 110 manages information, such as IV infusion information, for medical treatment of a patient and helps to reduce medication errors, improve quality of care, streamline clinical workflows and deliver potential cost savings.

The configurations for medical device network system 100 can vary widely in scope, depending on many factors. For instance, the size of the facility in which network system 100 is used may vary from a private practice, with a few medical devices 120, to a large hospital with a large number of devices 120 linked to the network. Similarly, the hardware associated with the system 100 can vary widely in configuration such as in the number of processors, the memory capacity, and processing capability of the hardware. Furthermore, the amount of transactions generated within the system 100 will depend on the operational needs of that particular facility. Thus, it would be desirable to be able to evaluate or to predict the performance of a particular configuration of a medical device management system to improve or optimize the configuration for a particular application or facility.

Figure 2:
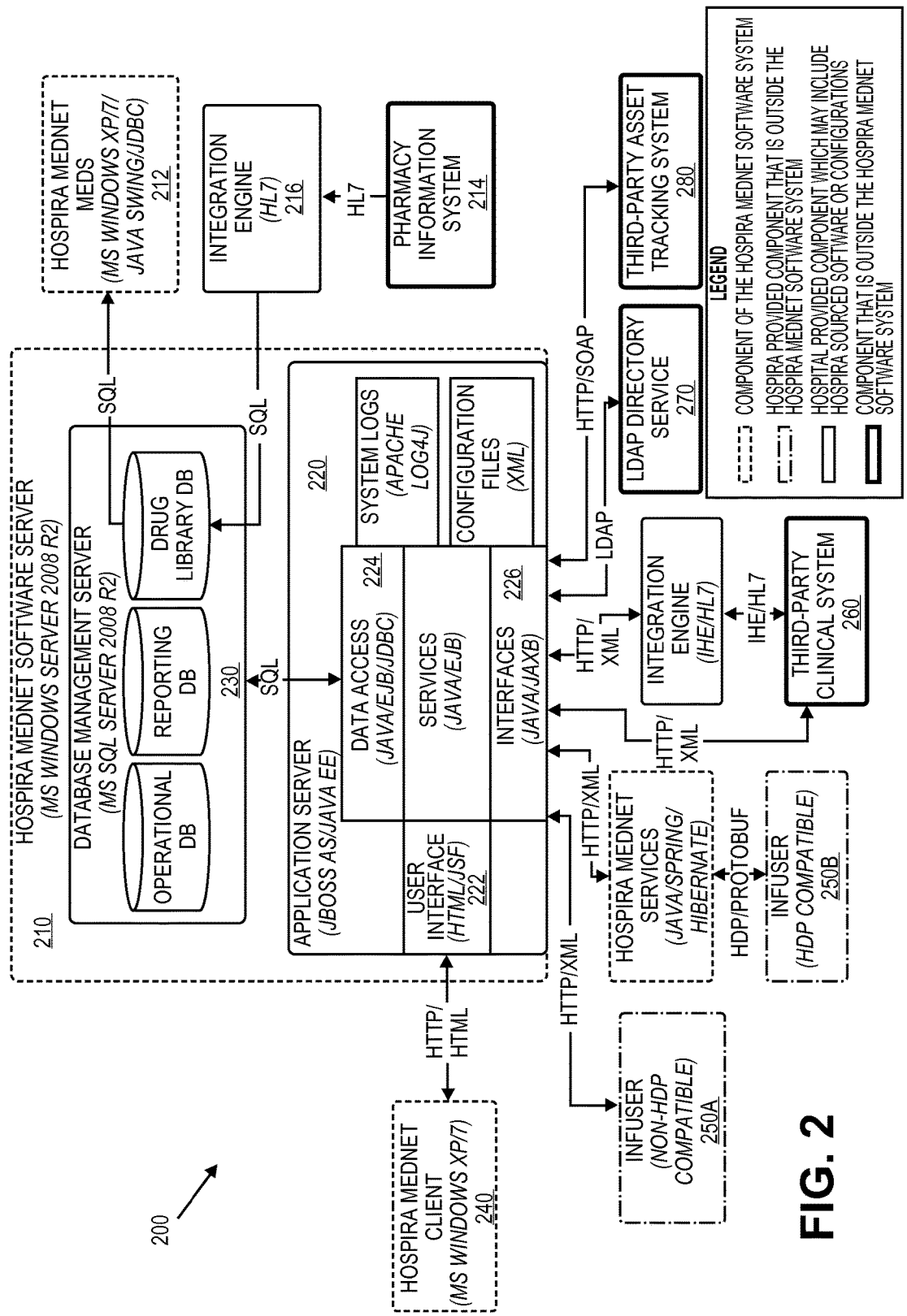
FIG. 2 is a technical block diagram of a medical device network, in one embodiment.

FIG. 2 is a technical block diagram of an embodiment of a medical device network system 200 that includes a medical device management component 210 (e.g., Hospira MedNet™ Software Server) having an application server 220 and a database management server 230. The application server 220 is a processing unit that may operate on, for example, a Moss™ or Java™ platform. The database management server 230 is in communication with the application server 220 and may be operate using any database programming language, for example, Structured Query Language (SQL). In this embodiment, database server 230 communicates with application server 220, with a drug library 212 (embodied here as Hospira MedNet™ Meds™), and/or with a pharmacy information system 214 via an integration engine 216. Thus, application server 220 manages data for medical devices 250a and 250b by accessing medication information from drug library 212 and pharmacy information system 214, and by interfacing with database 230 to retrieve and store data.

Application server 220 may include various components such as a user interface 222 for communicating with a client device 240, a data access component 224 to communicate with the database management server 230, and additional interfaces 226. Additional interfaces 226 may be configured to communicate with medical devices 250a/b, a third-party clinical system, a lightweight directory access protocol (LDAP) directory service 270, and a third-party asset tracking system 280. Medical devices 250a and 250b, embodied here as infusers, are outside the medical management system 210 and may interface with medical management system 210 using protocols that are health device profile (HDP) compatible or non-HDP compatible.

In FIG. 2, it can be seen that system 200 involves many mutually dependent programs that operate within an interdependent computer system. Since medical device management component 210, medical devices 250a/b, third-party clinical system 260, and other components may each be provided from different suppliers, the communication between all the various components may require interfacing between multiple program languages and communication protocols. For example, in FIG. 2, medical network system 200 accommodates SQL and Java™ languages, using HTTP/HTML, HTTP/XML, HTTP/SOAP and LDAP. Thus, the present systems and methods provide evaluation of medical device network system in which the system involves various platforms integrated together. Furthermore, the present systems and methods provide performance data for the overall network, and not just individual transactions. Data is gathered from the network and then processed and presented in a manner that allows a user to identify where bottlenecks or problems are occurring in the system.

The ability to evaluate or predict the performance of the system for various hardware and software configurations of a medical device system network, as described above, requires the integration of many parameters. Furthermore, identifying what parameters to evaluate, and how to integrate them to produce meaningful metrics can be burdensome. In the present disclosure, a performance index is described that not only derives an overall index value for a medical device network system, but also provides information on the relative contributions of the various performance parameters to the index. These relative contributions can be outputted, for example, in a graphical display to facilitate interpretation of the analysis by a user. The ability to view the impact of the performance parameters on the overall system enables a user to correct for detected problems. For example, a user can make adjustments to the medical device management software (e.g., Hospira MedNet™) to address specific problems. In one exemplary adjustment, a user may tune a SQL statement to help it improve the utilization of SQL to retrieve data, to further minimize latency around processing of messages. In other types of adjustments, the machine configuration within a computer may be altered to improve processing of messages, such as by modifying the hardware to increase the number of cores and threads. Thus, the evaluation can demonstrate value from a total cost of ownership standpoint, such as by identifying whether hardware for a particular network system needs to be changed to meet performance goals. For instance, the thread count, core count and memory of a system could be simulated and evaluated to accommodate a desired number of active objects running at the same time. The evaluations provided by the present methods can also enable performance comparisons of the impact that various medical device products have on system performance when connected to the network.

The performance index is generated by a monitoring software component that is in communication with the processing unit of the medical device management component. The monitoring software component is configured to i) monitor a number of messages between a number of medical devices and the processing unit, ii) process performance parameters to generate an overall performance index, and iii) generate an output that is viewable by a user, wherein the output includes relative contributions of each of the performance parameters to the overall performance index. The processing unit, the database software component, and the monitoring software component are housed on at least one computer. For example, in some embodiments the processing unit, the database software component and the monitoring software component may all be on separate computers. In other embodiments, the medical device management system processing unit and the database software component may be on one computer while the monitoring software component may be housed on a separate computer. In still further embodiments, the database software component, monitoring software component, and medical device management system processing unit are all located on separate computers.

Figure 3:
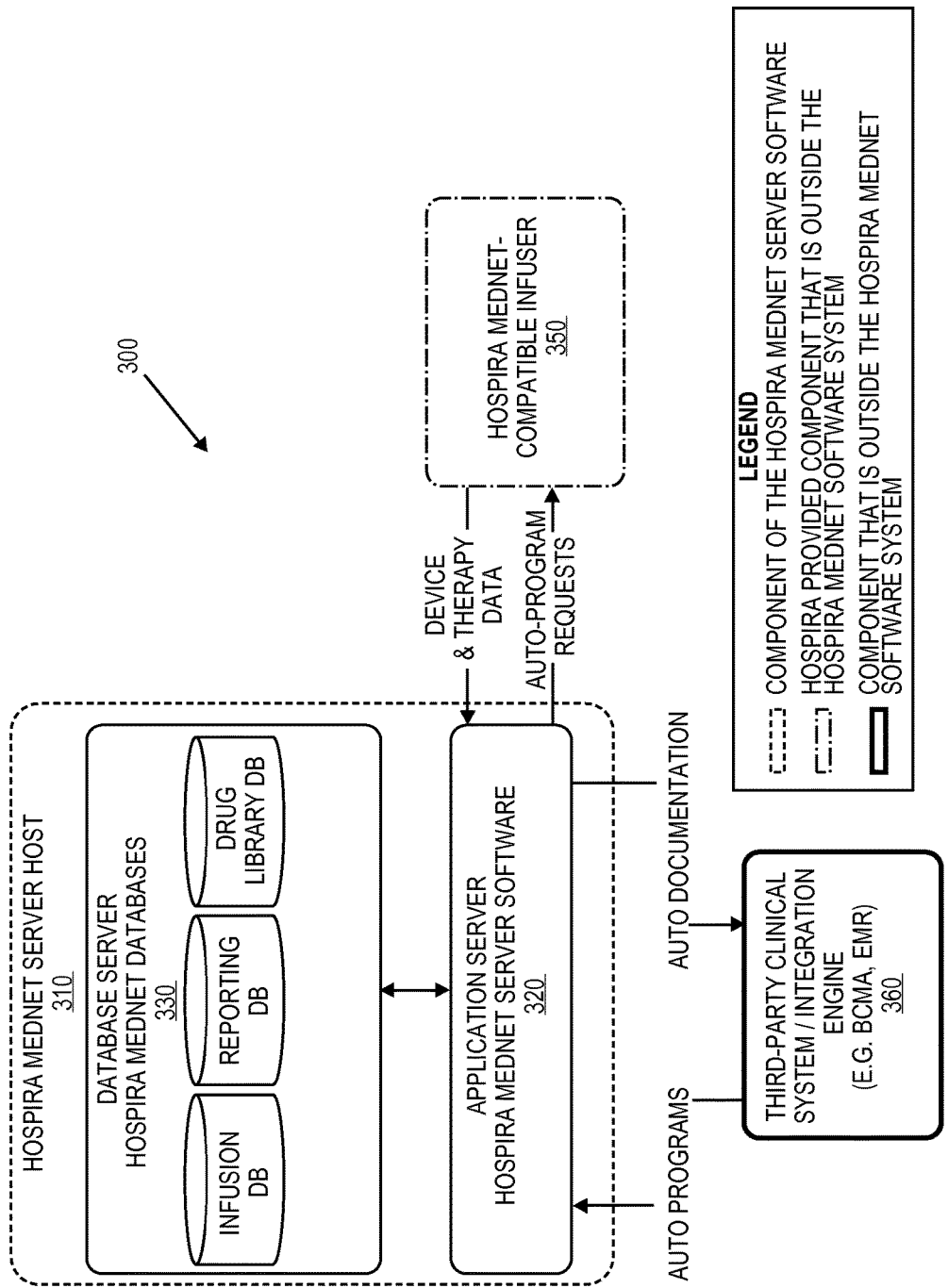
FIG. 3 is an exemplary block diagram of a single server configuration.

FIG. 3 depicts a diagram of a medical device network system 300 in a single server configuration. Similar to the previous figures, medical device network system 300 has a medical device management system 310 that includes an application server 320 and a database server 330. The application server 320 is a processing unit that is in communication with and is hosted together on a single server with database server 330. Application server 320 is also in communication with third-party clinical system/integration engine 360, as well as with medical device 350, which is embodied here as an infusion pump. Medical device 350 in diagram 300 may refer to one or more medical devices. Third-party clinical system 360 may provide auto programs to application server 320, and may receive auto documentation from application server 320. For instance, auto programs and auto documentation may assist in automatically programming the medical device 350 and charting of that information. Medical device 350 may receive auto program requests from application server 320, and may send device and therapy data to application server 320.

Figure 4:
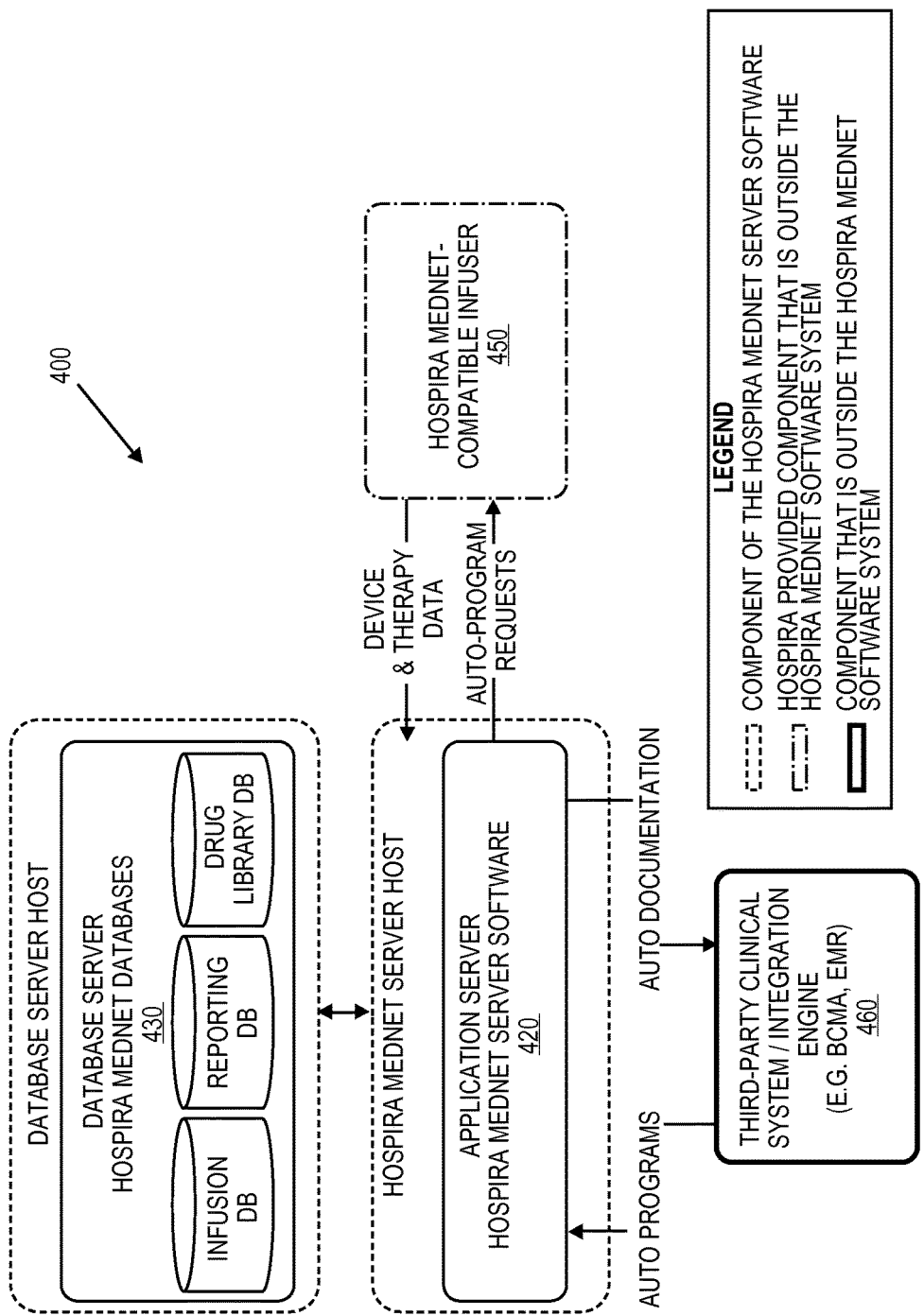
FIG. 4 is an exemplary block diagram of a distributed server configuration.

FIG. 4 is similar to FIG. 3 but for a medical device network system 400 having a distributed server configuration. That is, application server 420 is housed on a first computer, while database server 430 is on a second computer. Medical device 450 and third-party clinical system/integration engine 460 are the same as in FIG. 3.

In a network system, an important aspect of performance is the efficiency of processing messages through the system. This efficiency can be evaluated in many ways, depending on what measurement elements are utilized in the calculations. In the development of the present methods, parameters that affect performance were first identified, such as the central processing unit (CPU) consumption, processor queue length (PQL), disk queue length (DQL), and number of messages waiting in the medical device management software queue. For the purposes of this disclosure, the medical device management software will be described as a Java Messaging Service™ (JMS) system, although other types of programs may be substituted. After the performance parameters were identified, they were placed in order of importance. In one embodiment, the categories were ordered as JMS backlog, CPU, Memory usage, then Disk Input/Output. Based on their importance, a weighting percentage was distributed accordingly, for formulation of the performance index.

In some embodiments, the monitoring software component monitors actual traffic—that is, messages—within an operational medical device network system. The output results of performance index and contributions of the various performance parameters can then be used to identify, for instance, if the system has sufficient capacity for a certain number of medical devices, and where bottlenecks in system efficiency may be occurring. In other embodiments, the monitoring software simulates a number of medical devices that would be connected to the network, and simulates a number of messages generated by the medical devices. For such a simulation, the monitoring software enables a user to, for example, vary an anticipated number of medical devices connected to the network and the number of messages generated from the medical devices, to determine performance for projected configurations and optimize the system accordingly. For simulation scenarios, medical device 350 or 450 of FIGS. 3 and 4 may be a server that houses the monitoring software, external to the medical device management component, to simulate the load on the medical device network system during operation.

Performance parameters that are used for calculating system performance metrics involve factors related to the management software component, the database component, and the medical devices. In this disclosure, the following terminology shall be used:

CPU=Central Processing Unit or Processor of a machine.

DQL=Disk Queue Length. The average disk queue lengths represent the average number of both outstanding read and write requests at a given time.

HMSS=Hospira MedNet™ Server Suite, which represents a medical device management component, such as a software program housed on a first processing unit.

JMS=Java Messaging Service™. This is a set of interfaces for sending messages between two or more clients.

PQL=Processor Queue Length. The processor queue length is an indicator for the number of threads waiting to be processed.

SQL=Structured Query Language. In this disclosure, the term shall be used to reference the database server, although in other embodiments, other database languages may be substituted.

Perfmon=Windows™ Performance Monitor. This is a tool within the server that holds the Hospira Mednet™ software, that is used to collect the data and statistics of the network system. In other embodiments, other tools such Unix™ or Linux™ equivalents are possible.

The following variables for calculation of the performance index in this disclosure are described below:

HmssCPU=Observed HMSS CPU consumption. (CPU of the medical device management system) The consumption value is normalized to a percentage, such as 45% CPU Usage.

HmssPQL=Observed HMSS processor queue length. (PQL of the medical device management system) This value is taken from Perfmon. A maximum allowable value is set according to desired goals, such as number of cores*1.5. For example, if the CPU of the machine/VM have 4 cores, the maximum allowable queue length is 6. In other embodiments, the allowable tolerance may be 2-4 times the number of cores.

HmssDQL=Observed HMSS disk queue length. (DQL of the medical device management system) This value is taken from Perfmon. A maximum allowable value is set according to desired goals, such as a recommended queue length of less than 2. Higher values portend application performance degradation due to input/output (110) latency.

SqlCPU=Observed SQL (or other database) CPU consumption. This is the same as HmssCPU but measured for the database server.

SqlPQL=Observed SQL (or other database) processor queue length. This is the same as HmssPQL but measured for the database server.

SqlDQL=Observed SQL (or other database) disk queue length. This is the same as HmssDQL but measured for the database server.

NumOfJMSMsg=Observed number of JMS messages waiting to be processed. This value is taken from the JMS queue. A maximum allowable value is set according to desired goals, such as the maximum value being the Total Number of Infusers*10. For example, if a test consists of 100 infusers, JMS backlog of 1000 or more as measured at the end of the test is considered a failure.

MemUsage=HMSS (or other medical device management system) memory usage.

MaxIndexNumber=The total maximum value used for the Performance Index. In some embodiments, a lower value indicates better performance.

Figure 5:
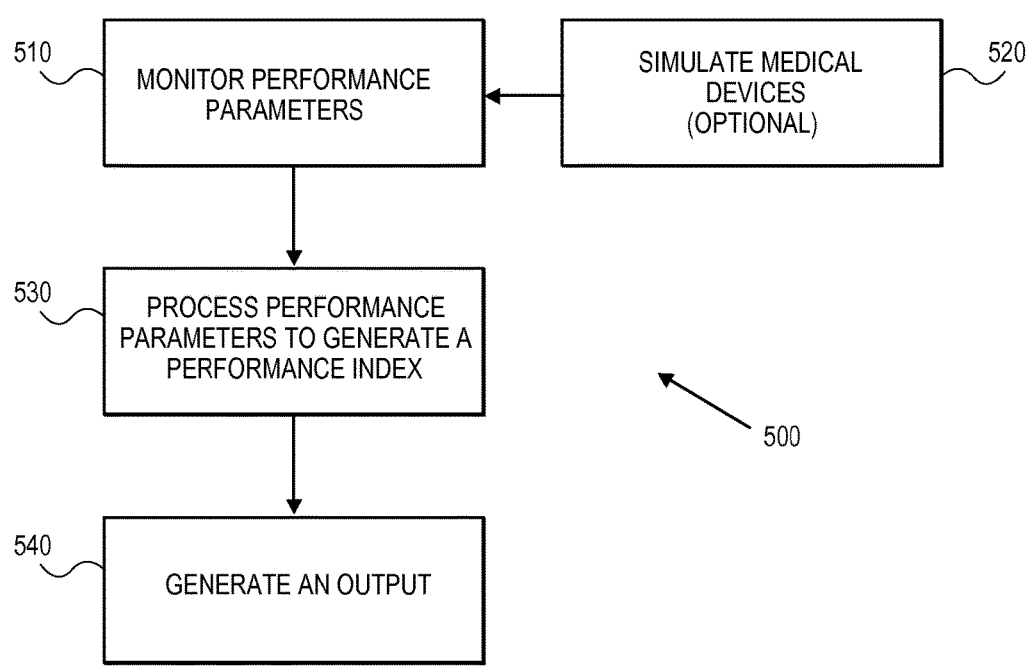
FIG. 5 shows an exemplary flow chart for a method of generating a performance index.

FIG. 5 shows an exemplary flow diagram 500 of the monitoring software in some embodiments. In step 510, performance parameters are monitored and gathered for evaluation. Step 510 may be conducted by custom software or by pre-packaged software. In one embodiment, step 510 utilizes Windows™ PerfMon to specify collector sets, such as queue length. Use of a program such as PerfMon can enable the monitoring software to be transportable to any type of server. The performance parameters may be gathered from a distributed network, such as a network including processing unit acting as a medical device management server, a database server, medical devices outside the medical device management server, and third-party interfaces. In step 520, the medical devices can optionally be simulated by the monitoring software program, such as by simulating the number of medical devices connected to the network, the type of devices, and the number of messages being generated by the devices. Because different types of devices, such as different models of infusions pumps, manifest traffic in different ways, the monitoring software can be programmed for a user to test different types and combinations of these devices. In other embodiments where performance of an actual physical system is being evaluated, step 520 may be omitted.

In step 530, the data is processed. For example, a set of data gathered within a specified time period may be aggregated for calculation of a set of performance metrics. Calculation of the performance parameters utilizes weighting factors associated with each performance parameter, as shall be described in more detail below, to generate an overall performance index. In step 540, an output is generated that is viewable by a user. The output includes relative contributions of the performance parameters to the overall performance index. For example, the output may take the form of numerical data tables, vertical or horizontal bar charts, such as stacked or grouped columns.

Calculation of performance parameters, such as in step 530 of FIG. 5, shall now be described in more detail. FIG. 6 shows an equation 600 for calculating a performance index, in one embodiment. In equation 600, the functions f(x) are defined by the entities to the right of that, indicated by curly braces. The equation can be generalized as $$\left( MaxIndexNumber * \sum \frac{NotedCategoryTakeResult}{MaxCategoryAllowedValue} * \text{Category Weighted \%} \right)$$

That is, the performance index is generated by summing entities for all the performance parameters, the entity for each performance parameter being the performance parameter value divided by a maximum allowed value and multiplied by the weighting factor associated with the performance parameter. For example, the first entity in equation 600 adds the maximum and average HMSS CPU data, divides it by the allowed value of 2, and multiplies the total by its weighting factor "HmssCPU %." The other performance parameters of SqlCPU, Number of JMS Messages, HmssPQL, HmssDQL, SqlDQL and Memory Usage are similarly calculated and summed. Note that the equation takes into account the server configuration format. Thus, for non-distributed scenarios the PQL and DQL are taken only once and the weighted percentage is combined. For example, if the system PQL=2.2 in a four core all-in-one machine, the formula would be (2.2/(4*1.5))*(0.125+0.1).

The weighting factor for each variable is carefully determined in relation to its contribution on system performance. A set of weighting factors, in some embodiments, is listed in Table 1 below, with a description of the weighting factors being presented in the subsequent paragraphs.

TABLE 1

| Variable | Weighting Factor |
|---|---|
| HmssCPU | 12.5% |
| HmssPQL | 12.5% |
| HmssDQL | 5% |
| SqlCPU | 12.5% |
| SqlPQL | 12.5% |
| SqlDQL | 5% |
| NumOfJMSMsg | 30% |
| MemUsage | 10% |
| MaxIndexNumber | 100% |

NumOfJMSMsg—This was deemed to have the largest weighting factor, such as about 30%, because the majority of the functionality of the Hospira MedNet™ software has to do with message processing and the timeliness of when the messages are processed. An example is processing status messages sent by the infuser and in turn sending updated statuses to a third party integrator. If there is a build up of messages and a messages stays in the queue longer than desired, by the time the message is sent out it is already stale.

The JMS message counter can also reveal issues within Hospira MedNet™ software that otherwise seems like Hospira MedNet™ is performing optimally. There are times when both CPU and PQL counters are low but JMS number is high. This is usually a clear indicator of a deadlock on either the JAVA side, SQL side or both.

CPU and PQL—These factors in Table 1 have intermediate weighting, such as about 12.5%. Raw processing and how long a process needs to wait for CPU time are the next factors. In an optimal operating environment when there are no blockages CPU is usually the limiting factor. The weighting is equally spread between CPU and PQL on both HMSS and SQL servers.

MemUsage—MemUsage has intermediate weighting, such as about 10%. This was deemed important because in order to have peak performance, having memory and not needing to use I/O is very crucial. A weighting factor of about 10% provides a good indicator if HMSS has a memory leak. Memory leak deals with memory clean-up and allocation, which can cause a system to fail if memory space becomes insufficient.

DQL—In the embodiment of Table 1 DQL has the smallest value, such as about 5%. This weighting will reveal any I/O bottlenecks in the system when running Hospira MedNet™ software, providing a relative indication of the importance of other problems.

Figure 7:
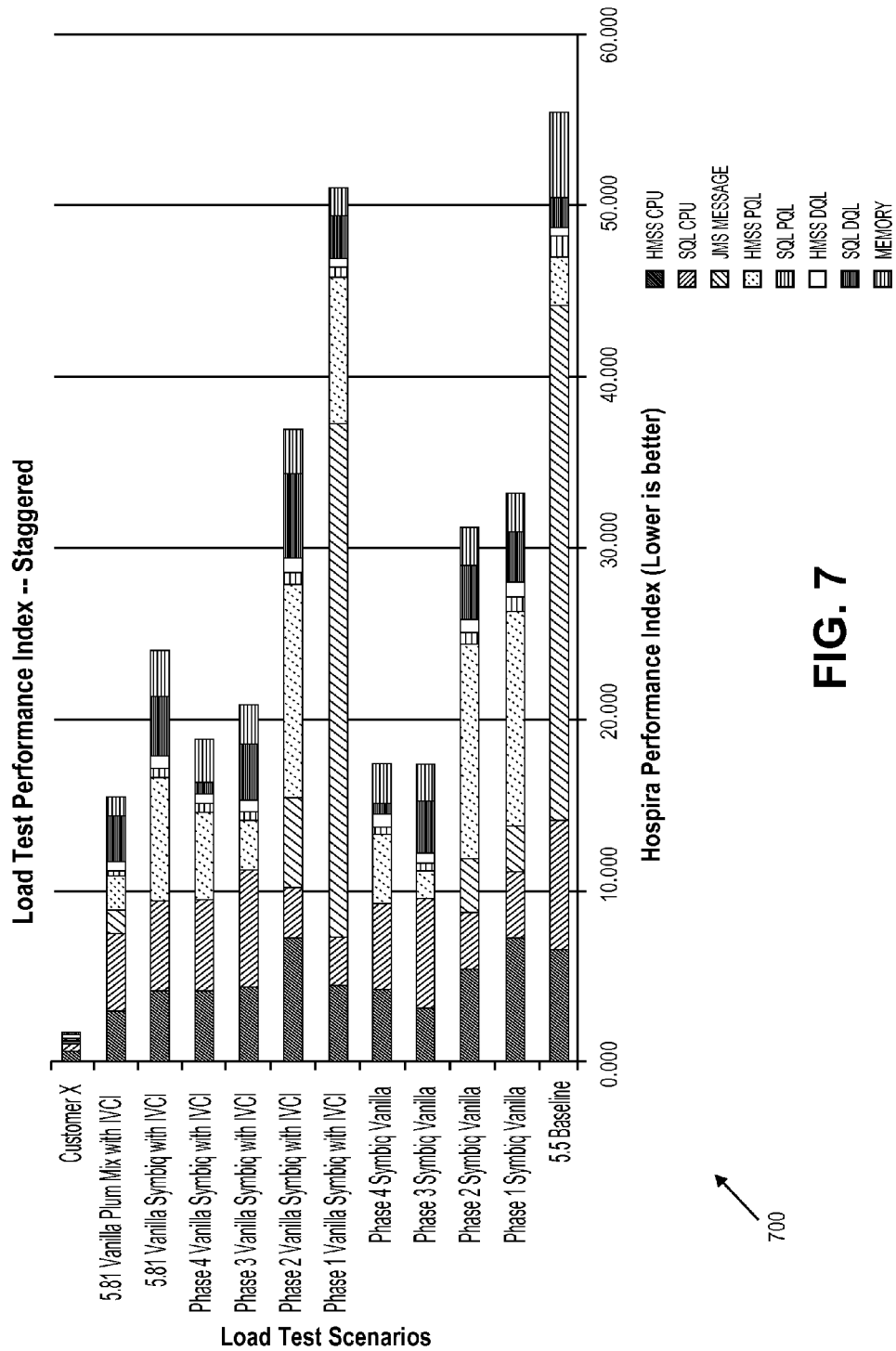
FIG. 7 provides an exemplary graphical output of a performance index analysis.
Figure 8:
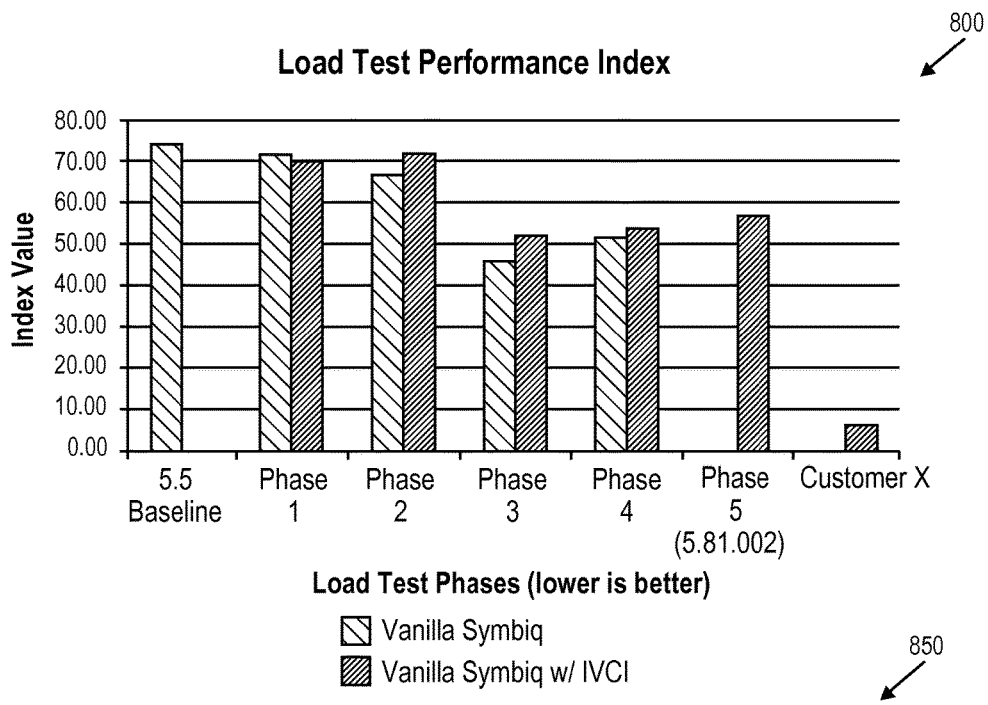
FIG. 8 provides another graphical output with tabular results of a performance index analysis.

FIGS. 7-8 show exemplary outputs generated by the performance index calculations. In FIG. 7, a stacked horizontal bar chart 700 shows relative contributions of various performance factors (HMSS CPU, SQL CPU, etc.), as indicated by the colored segments for each bar. The various bars represent performance component differentiation, such as from different models of infusers. In this sample chart, a comparison of the second and third bars from the top shows that the "5.81 Vanilla Plum Mix with IVCI" (IV with clinical integration) base Plum™ infuser model resulted in better system performance—that is, had a performance index that was smaller in value—than the "5.81 Vanilla Symbiq IVCI" or base Symbiq™ infuser model with IVCI. Looking at the sub-segments of these bars, it can be seen that the purple "HMSS PQL" component was a primary contributor to the worsened performance of the "Vanilla" Symbiq™ infuser with IVCI compared with the "Vanilla" Plum™ infuser Mix with IVCI. Consequently, a user could use these results to target how to improve processor queue length of the medical device management software (HMSS) when using the Vanilla Symbiq infuser model.

In FIG. 8, another graphical output is presented as a vertical bar chart 800 showing comparison of execution between functional differentiations; that is, between system configurations. For example, phases 1-5 represent changes made within the Hospira MedNet™ system, and the side-by-side bars of chart 800 show comparisons of the base or Vanilla Symbiq™ infuser with and without IVCI when run with the different phases. As can be seen, Vanilla Symbiq™ infuser with IVCI (blue bars) had higher performance index values and thus worse performance than Vanilla Symbiq™ infuser without IVCI (red bars). Table 850 shows the generated output in a numerical format, corresponding to the graphical output of chart 800.

Thus, FIGS. 7-8 show the ability of the performance index to evaluate the effect of different medical devices or management software configurations on the overall performance of a medical device network system. In other embodiments, the performance index could be used to compare different host configurations, with hardware and/or software adjustments. The various outputs may be displayed in different forms viewable by the user, such as, but not limited to graphical displays, numerical listings or tables, or text descriptions. The outputs may be generated as, for example, computer files, printed data, and/or displays on a computer monitor.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those of ordinary skill in the art, without departing from the scope of the present invention. Furthermore, those of ordinary skill in the art will appreciate that the foregoing description is by way of example only, and is not intended to limit the invention. Thus, it is intended that the present subject matter covers such modifications and variations.

What is claimed is:

1. A distributed network system comprising:
    a server configured to communicate over a network with a plurality of infusers and to transmit or receive infusion pump or infusion treatment data corresponding to the plurality of infusers;
    a database server in communication with the server, the database server configured to store the infusion pump or infusion treatment data; and
    one or more hardware processors in communication with the server and configured to:
        monitor communication between the server and the plurality of infusers, wherein the communication comprises network traffic corresponding to the transmission or receipt of the infusion pump or infusion treatment data,
        identify a plurality of performance parameters, the performance parameters comprising at least:
            a central processing unit (CPU) consumption of the server,
            a CPU consumption of the database server,
            a processor queue length (PQL) of the server,
            a PQL of the database server,
            a disk queue length (DQL) of the server,
            a DQL of the database server,
            a number of messages, from the plurality of infusers, waiting to be processed, and
            a memory usage,
        determine a weighting factor for each of the plurality of performance parameters, wherein each weighting factor is determined based at least in part on a degree to which a corresponding performance parameter contributes to performance of the system, wherein a largest weighting factor of the weighting factors corresponds to the number of messages waiting to be processed, a second largest weighting factor corresponds to one or more of the CPU consumption of the server, the CPU consumption of the database server, the PQL of the server, or the PQL of the database server, and the smallest weighting factor corresponds to at least one of the DQL of the server, the DQL of the database server, or the memory usage,
        generate a first performance index based at least in part on the plurality of performance parameters and the plurality of weighting factors, wherein the first performance index comprises a product of (a) a maximum index value and (b) a sum of each performance parameter value divided by a corresponding maximum allowed performance parameter value and multiplied by a corresponding weighting factor, wherein:
            a performance parameter value of the CPU consumption of the server corresponds to a sum of a maximum CPU consumption of the server and an average CPU consumption of the server,
            a performance parameter value of the CPU consumption of the database server corresponds to a sum of a maximum CPU consumption of the database server and an average CPU consumption of the database server,
            a performance parameter value of the PQL of the server corresponds to an average PQL of the server,
            a performance parameter value of the DQL of the server corresponds to the DQL of the server,
            a performance parameter value of the number of messages waiting to be processed corresponds to the number of messages waiting to be processed,
            a performance parameter value of the memory usage corresponds to the memory usage used, and
        cause a display to display an indication of the first performance index, wherein the indication of the first performance index identifies a relative contribution of each of the plurality of performance parameters to the first performance index, wherein an action to improve a performance of the system can be identified based at least in part on the indication of the first performance index, wherein the action comprises at least an adjustment to hardware or software corresponding the system, and
        generate a second performance index based at least in part on the first performance index and an indication of the action to improve the performance of the system,
        wherein a weighting factor for the number of messages from the infuser waiting to be processed is about 30%.

2. The system of claim 1, wherein:
    a weighting factor for the CPU consumption for the server is about 12.5%;
    a weighting factor for the PQL for the server is about 12.5%;
    a weighting factor for the DQL for the server is about 5%;
    a weighting factor for the CPU consumption for the database server is about 12.5%;
    a weighting factor for the PQL for the database server is about 12.5%;
    a weighting factor for the DQL for the database server is about 5%; and
    a weighting factor for the memory usage is about 10%.

3. The system of claim 1, wherein the one or more hardware processors are further configured to:
    receive an indication of the action identified by the user; and
    responsive to receiving the indication of the action, simulate communications between the plurality of infusers and the server, wherein the second performance index is further based at least in part on the simulated communications.

4. The system of claim 1, wherein the indication of the first performance index comprises at least one of an indication of an optimal number infusers for the system to achieve a desired system load or speed or an indication of an optimal configuration of the system to achieve the desired system load or speed.

5. The system of claim 1, wherein the one or more hardware processors are further configured to:
receive an indication of the action identified by the user; and
simulate at least some of the plurality of infusers, wherein the second performance index is further based at least in part on the simulated infusers.

6. The system of claim 1, wherein the action to improve the performance of the system comprises a combination of one or more of a modification to hardware to increase a number of cores, increase a number of threads, or increase memory.

7. The system of claim 1, wherein the action to improve the performance of the system comprises modifying a number of infusers in communication with the server.

8. The system of claim 1, wherein the action to improve the performance of the system comprises modifying a configuration of the system.

9. The system of claim 1, wherein the indication of the first performance index comprises a combination of one or more of a suggested hardware adjustment or a suggested software adjustment, and wherein the action to improve the performance of the system comprises the suggested hardware adjustment or the suggested software adjustment.

10. The system of claim 1, wherein the one or more hardware processors are further configured to receive the indication of the action to improve the performance of the system as user input.

11. A computer-implemented method comprising:
monitoring, using a one or more hardware processors in communication with a server, communications between a plurality of infusers and the server, wherein the server is configured to transmit or receive infusion pump or infusion treatment data corresponding to the plurality of infusers, and wherein the server is in communication with a database server that is configured to store the infusion pump or infusion treatment data;
identifying, using the one or more hardware processors, a plurality of performance parameters, wherein the plurality of performance parameters comprise at least:
a central processing unit (CPU) consumption of the server,
a CPU consumption of the database server,
a processor queue length (PQL) of the server,
a PQL of the database server, a disk queue length (DQL) of the server, a DQL of the database server,
a number of messages, from the plurality of infusers, waiting to be processed, and
a memory usage;
determining, using the one or more hardware processors, a weighting factor for each of the plurality of performance parameters, wherein a size of each weighting factor is determined based at least in part on a degree to which a corresponding performance parameter contributes to a performance of the system, wherein a largest weighting factor of the weighting factors corresponds to the number of messages from an infuser waiting to be processed;
determining a performance parameter value of the CPU consumption of the server comprising a sum of a maximum CPU consumption of the server and an average CPU consumption of the server;
determining a performance parameter value of the CPU consumption of the database server comprising a sum of a maximum CPU consumption of the database server and an average CPU consumption of the database server;
determining a performance parameter value of the PQL of the server comprising an average PQL of the server;
determining a performance value of the DQL of the server comprising the DQL of the server;
determining a performance parameter value of the number of messages waiting to be processed comprising the number of messages waiting to be processed;
determining a performance parameter value of the memory usage comprising the memory usage used;
generating, using the one or more hardware processors, a first performance index based at least in part on the weighting factor for each of the plurality of performance parameters and the plurality of performance parameters, wherein the first performance index comprises a product of (a) a maximum index value and (b) a sum of each performance parameter value divided by a corresponding maximum allowed performance parameter value and multiplied by a corresponding weighting factor;
causing a display to display an indication of the first performance index, wherein the indication of the first performance index identifies a relative contribution of each of the plurality of performance parameters to the first performance index, wherein an action to improve a performance of the system can be identified based at least in part on the indication of the first performance index, wherein the action comprises at least an adjustment to hardware or software corresponding the system, and
generating a second performance index based at least in part on the first performance index and an indication of the action to improve the performance of the system.

12. The system of claim 1, wherein:
a corresponding maximum allowed performance parameter value of the CPU consumption of the server corresponds to a sum of the maximum CPU consumption of the server and the maximum of the average CPU consumption of the server,
a corresponding maximum allowed performance parameter value of the CPU consumption of the database server corresponds to a sum of the maximum CPU consumption of the database server and the maximum of the average CPU consumption of the database server,
a corresponding maximum allowed performance parameter value of the PQL of the server is based upon a number of cores of the server,
a corresponding maximum allowed performance parameter value of the DQL of the server corresponds to a maximum DQL,
a corresponding maximum allowed performance parameter value of the number of messages waiting to be processed corresponds to a maximum number of messages waiting to be processed by the plurality of infusers, and
a corresponding maximum allowed performance value parameter of the memory usage corresponds to the maximum memory usage.

13. The method of claim 11, further comprising:
receiving an indication of the action identified by the user; and
simulating at least some of the plurality of infusers, wherein the second performance index is further based at least in part on the simulated infusers.

14. The method of claim 11, wherein:
a weighting factor for the CPU consumption for the server is about 12.5%;
a weighting factor for the PQL for the server is about 12.5%;
a weighting factor for the DQL for the server is about 5%;
a weighting factor for the CPU consumption for the database server is about 12.5%;
a weighting factor for the PQL for the database server is about 12.5%;
a weighting factor for the DQL for the database server is about 5%;
a weighting factor for the number of messages waiting to be processed is about 30%; and
a weighting factor for the memory usage is about 10%.

15. The method of claim 11, further comprising:
receiving an indication of the action identified by the user; and
responsive to receiving the indication of the action, simulating communications between the plurality of infusers and the server, wherein the second performance index is further based at least in part on the simulated communications.

16. The method of claim 11, wherein the indication of the first performance index comprises at least one of an indication of an optimal number of infusers for the system to achieve a desired system load or speed or an indication of an optimal configuration of the system to achieve the desired system load or speed.

17. The method of claim 11, wherein:
a corresponding maximum allowed performance parameter value of the CPU consumption of the server corresponds to a sum of the maximum CPU consumption of the server and the maximum of the average CPU consumption of the server,
a corresponding maximum allowed performance parameter value of the CPU consumption of the database server corresponds to a sum of the maximum CPU consumption of the database server and the maximum of the average CPU consumption of the database server,
a corresponding maximum allowed performance parameter value of the PQL of the server is based upon a number of cores of the server,
a corresponding maximum allowed performance parameter value of the DQL of the server corresponds to a maximum DQL,
a corresponding maximum allowed performance parameter value of the number of messages waiting to be processed corresponds to a maximum number of messages waiting to be processed by the plurality of infusers, and
a corresponding maximum allowed performance value parameter of the memory usage corresponds to the maximum memory usage.

18. A non-transitory machine-readable medium including instructions executable by a machine for generating a performance index, the instructions causing the machine to:
monitor communications between a plurality of infusers and a server, wherein the server is configured to transmit or receive infusion pump or infusion treatment data corresponding to the plurality of infusers, and wherein the server configured to communicate with a database server that is configured to store the infusion pump or infusion treatment data;
identify a plurality of performance parameters, wherein the plurality of performance parameters comprises at least:
a central processing unit (CPU) consumption of the server,
a CPU consumption of the database server,
a processor queue length (PQL) of the server,
a PQL of the database server,
a disk queue length (DQL) of the server,
a DQL of the database server,
a number of messages, from the plurality of infusers, waiting to be processed, and
a memory usage;
determine a weighting factor for each of the plurality of performance parameters, wherein a size of each weighting factor is determined based at least in part on a degree to which a corresponding performance parameter contributes to a performance of the system, wherein a largest weighting factor of the weighting factors corresponds to the number of messages from an infuser waiting to be processed;
generate a first performance index based at least in part on the plurality of performance parameters and the plurality of weighting factors wherein the first performance index comprises a product of (a) a maximum index value and (b) a sum of each performance parameter value divided by a corresponding maximum allowed performance parameter value and multiplied by a corresponding weighting factor, wherein:
a performance parameter value of the CPU consumption of the server corresponds to a sum of a maximum CPU consumption of the server and an average CPU consumption of the server,
a performance parameter value of the CPU consumption of the database server corresponds to a sum of a maximum CPU consumption of the database server and an average CPU consumption of the database server,
a performance parameter value of the PQL of the server corresponds to an average PQL of the server,
a performance parameter value of the DQL of the server corresponds to the DQL of the server,
a performance parameter value of the number of messages waiting to be processed corresponds to the number of messages waiting to be processed,
a performance parameter value of the memory usage corresponds to the memory usage used, and
cause a display to display an indication of the first performance index wherein the indication of the first performance index identifies a relative contributions of each of the plurality of performance parameters to the first performance index, wherein an action to improve a performance of the system can be identified based at least in part on the indication of the first performance index, wherein the action comprises at least an adjustment to hardware or software corresponding the system, and
generate a second performance index based at least in part on the first performance index and an indication of the action to improve the performance of the system.

19. The non-transitory machine-readable medium of claim 18 wherein:
a weighting factor for the CPU consumption for the server is about 12.5%;
a weighting factor for the PQL for the server is about 12.5%;

a weighting factor for the DQL for the server is about 5%;
a weighting factor for the CPU consumption for the database server is about 12.5%;
a weighting factor for the PQL for the database server is about 12.5%;
a weighting factor for the DQL for the database server is about 5%;
a weighting factor for the number of messages waiting to be processed is about 30%; and
an weighting factor for the memory usage is about 10%.

20. The non-transitory machine-readable medium of claim 18 wherein the instructions are further configured to cause the machine to receive an indication of the action identified by the user and, responsive to receiving the indication of the action, simulate communications between the plurality of infusers, wherein the second performance index is further based at least in part on the simulated communications.

21. The non-transitory machine-readable medium of claim 18, wherein the indication of the first performance index comprises at least one of an indication of an optimal number of infusers for the system to achieve a desired system load or speed or an indication of an optimal configuration of the system to achieve the desired system load or speed.

22. The non-transitory machine-readable medium of claim 18, wherein the instructions are further configured to cause the machine to:
receive an indication of the action identified by the user; and
simulate at least some of the plurality of infusers, wherein the second performance index is further based at least in part on the simulated infusers.

23. The non-transitory machine-readable medium of claim 18, wherein:
a corresponding maximum allowed performance parameter value of the CPU consumption of the server corresponds to a sum of the maximum CPU consumption of the server and the maximum of the average CPU consumption of the server,
a corresponding maximum allowed performance parameter value of the CPU consumption of the database server corresponds to a sum of the maximum CPU consumption of the database server and the maximum of the average CPU consumption of the database server,
a corresponding maximum allowed performance parameter value of the PQL of the server is based upon a number of cores of the server,
a corresponding maximum allowed performance parameter value of the DQL of the server corresponds to a maximum DQL,
a corresponding maximum allowed performance parameter value of the number of messages waiting to be processed corresponds to a maximum number of messages waiting to be processed by the plurality of infusers, and
a corresponding maximum allowed performance value parameter of the memory usage corresponds to the maximum memory usage.

* * * * *